United States Patent [19]

Lunn et al.

[11] Patent Number: 5,552,426
[45] Date of Patent: Sep. 3, 1996

[54] METHODS FOR TREATING A PHYSIOLOGICAL DISORDER ASSOCIATED WITH β-AMYLOID PEPTIDE

[75] Inventors: William H. W. Lunn; James A. Monn, both of Indianapolis; Dennis M. Zimmerman, Mooresville, all of Ind.

[73] Assignee: Eli Lilly and Company, Indianapolis, Ind.

[21] Appl. No.: 235,400

[22] Filed: Apr. 29, 1994

[51] Int. Cl.⁶ .............. A61K 31/415; C07D 235/18; C07D 235/08
[52] U.S. Cl. .............. 514/394; 514/395; 548/304.4; 548/306.4; 548/306.7; 548/309.7; 548/310.1; 548/310.4; 548/310.7
[58] Field of Search .............. 514/394, 395; 548/304.4, 304.7, 305.1, 305.4, 306.4, 306.7, 309.7, 310.1, 310.4, 310.7

[56] References Cited

U.S. PATENT DOCUMENTS

| | | | |
|---|---|---|---|
| 5,137,906 | 8/1992 | Chiu et al. | 514/394 |
| 5,187,159 | 2/1993 | Greenlee et al. | 514/81 |

FOREIGN PATENT DOCUMENTS

| | | |
|---|---|---|
| 0563001 | 6/1993 | European Pat. Off. . |
| 4142366 | 6/1993 | Germany . |
| 4000074 | 2/1989 | Japan . |

*Primary Examiner*—José G. Dees
*Assistant Examiner*—Deborah Lambkin
*Attorney, Agent, or Firm*—Paul J. Gaylo; David E. Boone

[57] ABSTRACT

This invention provides substituted benzimidazoles which are useful in treating or preventing conditions associated with β-amyloid peptide. Some such conditions associated with β-amyloid peptide include Alzheimer's Disease, Down's Syndrome and amyloidosis of the Dutch type.

6 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Asp Ala Glu Phe Arg His Asp Ser Gly Tyr Glu Val His His Gln Lys
   1               5                   10                  15

Leu Val Phe Phe Ala Glu Asp Val Gly Ser Asn Lys Gly Ala Ile Ile
                   20                  25                  30

Gly Leu Met Val Gly Gly Val Val Ile Ala Thr
                   35                  40

( 2 ) INFORMATION FOR SEQ ID NO:2:

( i ) SEQUENCE CHARACTERISTICS:
      ( A ) LENGTH: 40 amino acids
      ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:2:

| Asp | Ala | Glu | Phe | Arg | His | Asp | Ser | Gly | Tyr | Glu | Val | His | His | Gln | Lys |
|---|---|---|---|---|---|---|---|---|---|---|---|---|---|---|---|
| 1 | | | | 5 | | | | | 10 | | | | | 15 | |

| Leu | Val | Phe | Phe | Ala | Glu | Asp | Val | Gly | Ser | Asn | Lys | Gly | Ala | Ile | Ile |
|---|---|---|---|---|---|---|---|---|---|---|---|---|---|---|---|
| | | | 20 | | | | | 25 | | | | | 30 | | |

| Gly | Leu | Met | Val | Gly | Gly | Val | Val |
|---|---|---|---|---|---|---|---|
| | | 35 | | | | | 40 |

METHODS FOR TREATING A PHYSIOLOGICAL DISORDER ASSOCIATED WITH β-AMYLOID PEPTIDE

BACKGROUND OF THE INVENTION

Alzheimer's disease is a degenerative disorder of the human brain. Clinically, it appears as a progressive dementia. Its histopathology is characterized by degeneration of neurons, gliosis, and the abnormal deposition of proteins in the brain. Proteinaceous deposits (called "amyloid") appear as neurofibrillary tangles, amyloid plaque cores, and amyloid of the congophilic angiopathy. [For a review, see, D. J. Selkoe, *Neuron*, 6:487–498 (1991)]

While there is no general agreement as to the chemical nature of neurofibrillary tangles, the major constituent of both the amyloid plaque cores and the amyloid of the congophilic angiopathy has been shown to be a 4500 Dalton protein originally termed β-protein or amyloid A4. Throughout this document this protein is referred to as β-amyloid peptide or protein.

β-amyloid peptide is proteolytically derived from a transmembrane protein, the amyloid precursor protein. Different splice forms of the amyloid precursor protein are encoded by a widely expressed gene. see, e.g., K. Beyreuther and B. Müller-Hill, *Annual Reviews in Biochemistry*, 58:287–307 (1989). β-amyloid peptide consists, in its longest forms, of 42 or 43 amino acid residues. J. Kang, et al., *Nature (London)*, 325:733–736 (1987). These peptides, however, vary as to their amino-termini. C. Hilbich, et al., *Journal of Molecular Biology*, 218:149–163 (1991).

Because senile plaques are invariably surrounded by dystrophic neurites, it was proposed early that β-amyloid peptide is involved in the loss of neuronal cells that occurs in Alzheimer's disease. B. Yankner and co-workers were the first to demonstrate that synthetic β-amyloid peptide could be neurotoxic in vitro and in vivo. B. A. Yankner, et al., *Science*, 245:417 (1989); See, also, N. W. Kowall, et al., *Proceedings of the National Academy of Sciences, U.S.A.*, 88:7247 (1991). Other research groups, however, were unable to consistently demonstrate direct toxicity with β-amyloid peptide. See, e.g., *Neurobiology of Aging*, 13:535 (K. Kosik and P. Coleman, eds. 1992). Even groups receiving β-amyloid peptide from a common source demonstrate conflicting results. P. May, et al., *Neurobiology of Aging*, 13:605–607 (1992).

In addition to Alzheimer's disease, Down's syndrome is also characterized by an accumulation of β-amyloid peptide. In patients suffering from Down's syndrome the β-amyloid peptide is the primary constituent of senile plaques and cerebrovascular deposits.

Because of the debilitating effects of Alzheimer's disease, Down's syndrome, and these other conditions associated with amyloidogenic peptides and proteins there continues to exist a need for effective treatments. This invention provides compounds efficacious in the treatment and prevention of these disorders.

SUMMARY OF THE INVENTION

This invention describes a method of treating or preventing a physiological disorder associated with β-amyloid peptide in a mammal which comprises administering to a mammal in need of said treatment an effective amount of a compound of Formula I

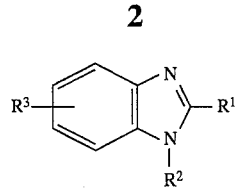

wherein:

$R^1$ is hydrogen, $C_1$–$C_{12}$ alkyl, $C_1$–$C_6$ alkoxy, phenyl, $C_3$–$C_8$ cycloalkyl, naphthyl, heterocyclic, unsaturated heterocyclic, phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1$–$C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-, any one of which phenyl, naphthyl, heterocyclic, $C_3$–$C_8$ cycloalkyl, or unsaturated heterocyclic groups may be optionally substituted with one, two, or three moieties independently selected from group consisting of heterocyclic-($C_1$–$C_6$ alkylidenyl)-, unsaturated heterocyclic-($C_1$–$C_6$ alkylidenyl)-, hydroxy, halo, $C_1$–$C_6$ alkyl, $C_1$–$C_6$ alkoxy, trifluoromethyl, nitro, amino, cyano, $C_1$–$C_6$ alkylamino, and $C_1$–$C_6$ alkylthio;

$R^2$ is hydrogen, $C_1$–$C_{12}$ alkyl, $C_1$–$C_6$ alkoxy, phenyl, $C_3$–$C_8$ cycloalkyl, naphthyl, heterocyclic, unsaturated heterocyclic, phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1$–$C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-, any one of which phenyl, naphthyl, heterocyclic, $C_3$–$C_8$ cycloalkyl, or unsaturated heterocyclic groups may be optionally substituted with one, two, or three moieties independenly selected from group consisting of phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-, hydroxy, halo, $C_1$–$C_6$ alkyl, $C_1$–$C_6$ alkoxy, trifluoromethyl, nitro, amino, cyano, $C_1$–$C_6$ alkylamino, and $C_1$–$C_6$ alkylthio;

$R^3$ is hydrogen, nitro, $C_1$–$C_6$ alkanoyl, amino, $C_1$–$C_6$ alkyl, $C_1$–$C_6$ alkoxy, $C_3$–$C_8$ cycloalkyl, heterocyclic, unsaturated heterocyclic, halo, $C_1$–$C_6$ alkylthio, hydroxy-($C_1$–$C_6$ alkylidenyl)-, hydroxy-($C_1$–$C_6$ alkylidenyl) amino-, $R^4R^5N$—, $R^4R^5N$-($C_1$–$C_6$ alkylidenyl)-, $R^4R^5N$-($C_1$–$C_6$ alkoxy)-, hydroxy-($C_1$–$C_6$ alkyl)-, heterocyclic-($C_1$–$C_6$ alkoxy)-, amino($C_1$–$C_6$ alkylidenyl)-, or trifluoromethyl, where $R^4$ and $R^5$ are independently selected from the group consisting of $C_1$–$C_6$ alkyl, $C_1$–$C_6$ alkoxy, $C_1$–$C_6$ alkanoyl, aryl, heterocyclic, unsaturated heterocyclic, aryl($C_1$–$C_6$ alkylidenyl)-, heterocyclic ($C_1$–$C_6$ alkylidenyl)-, unsaturated heterocyclic ($C_1$–$C_6$ alkylidenyl)-, and hydrogen or $R^4$ and $R^5$ combine to form $C_3$–$C_8$ cycloalkyl, any one of which alkyl or alkoxy groups may be substituted with one or more halo, amino, or nitro, and any one of which aryl, unsaturated heterocyclic, or heterocyclic groups may be substituted with one, two, or three moieties independently selected from group consisting of hydroxy, halo, $C_1$–$C_6$ alkyl, $C_1$–$C_6$ alkoxy, trifluoromethyl, nitro, amino, cyano, $C_3$–$C_8$ cycloalkyl, $C_1$–$C_6$ alkylamino, and $C_1$–$C_6$ alkylthio;

with the proviso that not more than one of $R^1$ and $R^2$ may be hydrogen;

or a pharmaceutically acceptable salt thereof.

DETAILED DESCRIPTION AND PREFERRED EMBODIMENTS

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_{12}$ alkyl" refers to straight or branched, monovalent, saturated aliphatic chains of 1 to 12 carbon atoms and includes, but is not limited to, methyl, ethyl, propyl, isopropyl, butyl, isobutyl, t-butyl, pentyl, isopentyl, and hexyl. The term "$C_1$–$C_{12}$ alkyl" includes within its definition the term "$C_1$–$C_6$ alkyl".

"Aryl" as used herein refers to phenyl or naphthyl or a substituted derivative thereof;

"Halo" represents chloro, fluoro, bromo or iodo.

"Hydroxy($C_1$–$C_6$)alkyl" represents a straight or branched alkyl chain having from one to six carbon atoms with an hydroxy group attached to it. Typical hydroxy($C_1$–$C_6$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl and the like.

"$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio and the like. The term "$C_1$–$C_6$ alkylthio" includes within its definition the term "$C_1$–$C_4$ alkylthio".

"$C_1$–$C_6$ alkylamino" represents a straight or branched alkylamino chain having from one to six carbon atoms attached to an amino group. Typical $C_1$–$C_6$ alkylamino groups include methylamino, ethylamino, propylamino, isopropylamino, butylamino, sec-butylamino and the like.

"$C_1$–$C_6$ alkylidenyl" refers to a straight or branched, divalent, saturated aliphatic chains of 1 to 6 carbon atoms and includes, but is not limited to, methylenyl, ethylenyl, propylenyl, isopropylenyl, butylenyl, isobutylenyl, t-butylenyl, pentylenyl, isopentylenyl, and hexylenyl.

The term "heterocycle" represents a stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

The term "unsaturated heterocycle" represents a stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, and tetrahydroisoquinolinyl.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include acetyl, propanoyl, isopropanoyl, butanoyl, t-butanoyl, pentanoyl, hexanoyl, 3-methylpentanoyl and the like.

"$C_3$–$C_8$ cycloalkyl" represents a saturated hydrocarbon ring structure containing from three to eight carbon atoms which is unsubstituted. Typical $C_3$–$C_8$ cycloalkyl groups include cyclopropyl, cyclopentyl, cyclohexyl, cycloheptyl, and cyclooctyl.

The term "hydroxy-protecting groups" as used herein refers to substitents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of these groups may be found in T. W. Greene and P. G. M. Wuts, "Protective Groups in Organic Synthesis (1991) at Chapter 3.

The compounds used in the method of the present invention may have one or more asymmetric centers. As a consequence of these chiral centers, the compounds of the present invention may occur as racemates, mixtures of enantiomers and as individual enantiomers, as well as diastereomers and mixtures of diastereomers. All asymmetric forms, individual isomers and combinations thereof, are within the scope of the present invention.

As noted supra, this invention includes methods employing the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses methods employing the the pharmaceutically acceptable solvates of the compounds of Formula I as well as the solvates of the compounds of Formula II. Many of the compounds of Formulae I and II can combine with solvents such as water, methanol, ethanol and acetonitrile to form pharmaceutically acceptable solvates such as the corresponding hydrate, methanolate, ethanolate and acetonitrilate.

The compounds of the present invention are derivatives of benzimidazole which are named and numbered according to the Ring Index, The American Chemical Society, as follows.

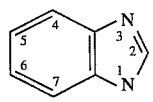

The preferred methods of this invention employ those compounds of Formula I wherein:

a) $R^1$ is phenyl, naphthyl, heterocyclic, unsubstituted heterocyclic, or substituted derivatives thereof;

b) $R^2$ is phenyl, heterocyclic, unsaturated heterocyclic, phenyl($C_1$–$C_6$ alkylidenyl)-, heterocyclic ($C_1$– $C_6$ alkylidenyl)-, unsaturated heterocyclic($C_1$–$C_6$ alkylidenyl)-, or substituted derivatives thereof;

c) $R^3$ is $R^4R^5N$-($C_1$–$C_6$ alkylidenyl)-, $C_1$–$C_6$ alkanoyl, $C_1$–$C_4$ alkoxy, imidazole, amino-($C_1$–$C_6$ alkylidenyl, hydroxy-($C_1$–$C_6$ alkylidenyl) amino-, heterocyclic-($C_1$–$C_6$ alkoxy)-, $R^4R^5N$-($C_1$–$C_6$ alkoxy)-, or hydroxy;

d) $R^3$ is at the 5 or 6 position of the benzimidazole.

The especially preferred methods of this invention employ those compounds of Formula I wherein:

a) $R^1$ is phenyl or naphthyl substituted with one or more electron donating, lipophilic substituents;

b) $R^2$ is substituted benzyl or substituted phenyl;

c) $R^3$ is $R^4R^5N$-($C_1$–$C_6$ alkylidenyl)-, heterocyclic-($C_1$–$C_6$ alkoxy)-, $R^4R^5N$-($C_1$–$C_6$ alkoxy)-, or unsaturated heterocyclic ($C_1$–$C_6$ alkylidenyl)-; and d) $R^3$ is at the 6 position of the benzimidazole.

In the scientific literature derivatives of benzimidazole are already known to possess different biological activities, such as analgesic and antiinflammatory activity (Japan Kokai 75,126,682; U.S. Pat. No. 4,925,853), gastric antisecretory activity (European Patent Publication 246,126), antihistaminic activity (U.S. Pat. No. 4,200,641 and 5,182,280), dopaminergic and andrenergic activity (U.S. Pat. No. 4,925, 854), bronchodilatory activity, and growth promotion (U.S. Pat. No. 4,960,783).

The compounds of Formula I can be prepared by processes known in the literature. See, e.g., G. W. H. Cheeseman and R. F. Cookson, "The Chemistry of Heterocyclic Compounds" (A. Weissberger, et al., eds. 1979). The usual process for the preparation of the compounds of Formula I is by cyclization of an appropriately substituted o-phenylenediamine of Formula III

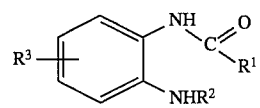

in a solvent or solvent mixture. It is generally preferred that the solvent or solvent mixture be heated, preferably to the boiling point of the solvent. Suitable solvents include ethanol, isopropanol, glacial acetic acid, benzene, toluene, chlorobenzene, glycol, ethylene glycol, dimethyl ether, diethyl ether, dimethylformamide, chloroform, ethyl acetate, and the like. It is generally preferred to add a condensation agent such as phosphorous oxychloride, thionyl chloride, p-toluenesulfonic acid, hydrochloric acid, sulfuric acid, phosphoric acid, polyphosphoric acid, phosphorous pentoxide, methanesulfonyl hydroxide, methanesulfonyl chloride, and the like. The cyclization reaction may also optionally be performed in the presence of a base such as sodium hydroxide, sodium mesylate, or potassium tert-butylate.

In those compounds in which $R^2$ is phenyl a derivative of N-phenyl-o-phenylenediamine was used as the starting material for the cyclization reaction. The examples infra provide sufficient guidance in the preparation of those compounds of Formula I wherein $R^3$ is hydrogen.

Those compounds of Formula I wherein $R^3$ is not hydrogen, can be prepared by methods taught in the literature. For example, the compounds of this invention wherein $R^3$ is $C_2$–$C_6$ alkanoyl can be prepared from the appropriate keto o-phenylenediamine of the formula

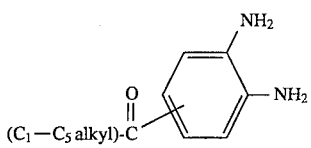

by methods known in the benzimidazole art such as the procedures described in U.S. Pat. No. 4,401,817, issued Aug. 30, 1983, which is herein incorporated by reference. The method of preparation involves the ammonolysis and reduction of a 4-halo-3-nitrophenyl ketone which is prepared by the Friedel-Crafts reaction of either a 4-halo-3-nitrobenzoyl chloride with an appropriate hydrocarbon or a halobenzene with an appropriate acid chloride followed by aromatic nitration.

Alternatively, the keto benzimidazole reactants can be prepared from acetanilide by a Friedel-Crafts acylation with the appropriate derivative of $C_2$–$C_6$ alkanoic acid. The resulting 4-keto acetanilide is nitrated to give a 2-nitro-4-ketoacetanilide. The acetanilide is hydrolyzed to give a 2-nitro-4-ketoaniline, which can then be catalytically hydrogenated to yield a 4-keto-o-phenylenediamine which can then be ring closed to provide the 5 or 6-substituted benzimidazole.

Those compounds of Formula III wherein $R^3$ is a substituted alkyl or alkylidenyl may be prepared by means of a Friedel-Crafts alkylation with the appropriate derivative of the $R^3$ moiety using standard procedures, usually employing an alkyl halide or an olefin in the presence of a catalyst such as aluminum chloride, aluminum bromide or another Lewis acid.

An alternative strategy for preparing those compounds of Formula I wherein $R^3$ is $C_1$–$C_6$ alkoxy, $R^4R^5N$-($C_1$–$C_6$ alkoxy)-, or heterocyclic-($C_1$–$C_6$ alkoxy)-, or a substituted derivative thereof, involves first reacting a 3-nitro-4-aminophenol with an acyl halide in the presence of a base

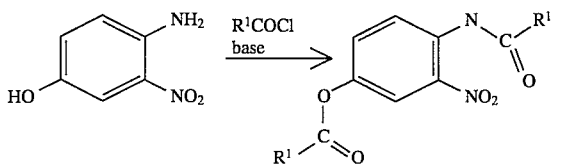

to get substitution of the primary amine as well as substitution of the hydroxy group, the ester moiety serving as a hydroxy-protecting group for subsequent reactions. In the next step of this synthesis the nitro group is then reduced to an amino group, usually by catalytic hydrogenation.

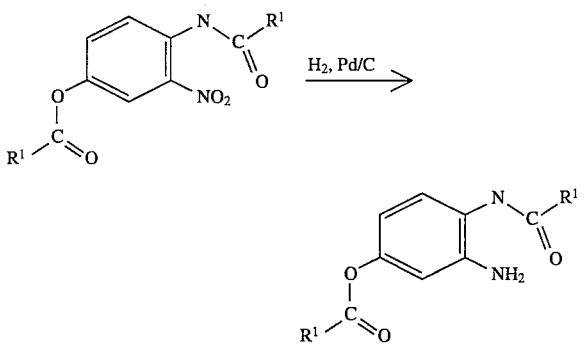

The primary amine of the above compound is then substituted, usually using an aldehyde, such as benzaldehyde or a substituted derivative thereof, followed by hydrogenation, if necessary. In an alternative embodiment, those compounds of Formula I in which $R^2$ is alkyl or substituted alkyl may be produced by alkylation of an aromatic amine with alkyl halide or tosylate, or the like, in the presence of a suitable base, such as trialkylamine, potassium carbonate, 1,8-diazabicyclo[5.4.0]undec-7-ene (DBU), and the like.

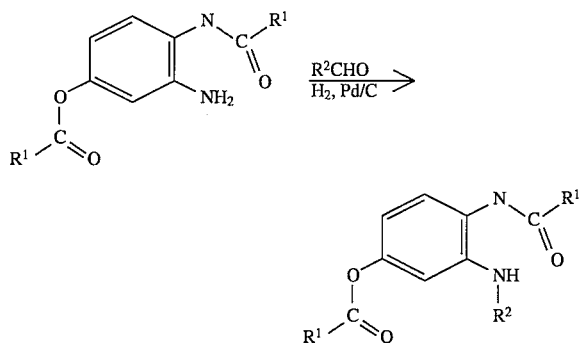

Cyclization of this substituted phenylenediamine is then performed as described supra, followed by cleavage of the ester group protecting the hydroxy group at the 6-position of the benzimidazole. Suitable cyclization catalysts include phosphorous oxychloride, thionyl chloride, phosphorous pentoxide, phosphorous pentachloride, and other like strong dehydrating agents.

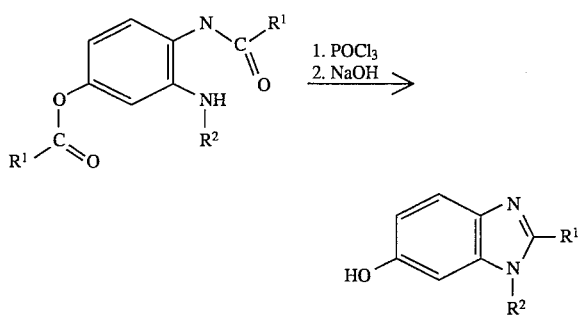

A preferred method of cleaving this ester is by incubation of the intermediate in a basic solution, such as 1N sodium hydroxide, or a weaker base such as potassium carbonate. The hydroxy group at the 6-position is then substituted using an alkyl or aryl halide, resulting in a compound of Formula I.

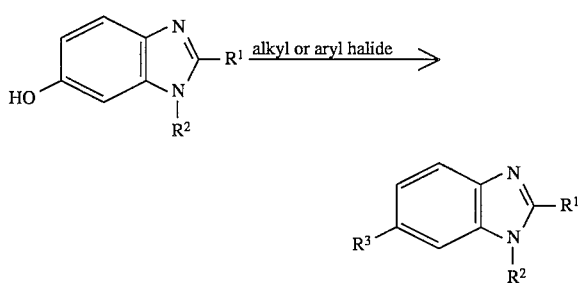

The skilled artisan understands that compounds of Formula I substituted at the 5-position of the benzimidazole can be prepared as described above by employing 3-amino-4-nitrophenol as the starting material instead of the 3-nitro-4-aminophenol shown supra.

Those compounds of Formula I wherein $R^2$ is alkyl or substituted alkyl may alternatively be prepared by the direct alkylation of a benzimidazole wherein the nitrogen at the 1-position is substituted with a hydrogen. This type of alkylation is usually performed by the reaction of the benzimidazole with an alkyl halide in the presence of a strong base, such as sodium hydride. This reaction is usually performed in a polar aprotic solvent, such as N,N-dimethylformamide, dimethyl sulfoxide, dimethylacetamide, hexamethylphosphoric triamide, and the like.

The following examples further illustrate the preparation of the compounds of Formula I. The examples are illustrative only and are not intended to limit the scope of the invention in any way. The designations "NMR", "IR", and "MS" in an example indicate that the nuclear magnetic resonance spectrum (NMR), the infrared absorption spectrum (IR), or the mass as determined by mass spectrometry (MS) were consistent with the desired compound.

EXAMPLE 1

Synthesis of 1,2-diphenylbenzimidazole

N-phenyl-o-phenylenediamine (10 mmol, 1.84 grams) was added to diethyl ether (100 ml) and stirred at room temperature as benzoyl chloride (10 mmol, 1.41 g) was added dropwise (a precipitate formed after about one half of the benzoyl chloride was added). After addition of the benzoyl chloride, the solution was stirred at room temperature for about 15 minutes. The reaction mixture was partitioned between aqueous sodium hydroxide and diethyl ether. The organic layer was removed and the aqueous layer was extracted with ethyl acetate (3×100 ml). The organic fractions were combined and dried over magnesium sulfate. The magnesium sulfate was filtered out and the solvent removed in vacuo to yield a red/brown solid (2.88 g, 99.8%) which was suitable for use in the cyclization reaction. NMR, mp 136°–137° C.

A solution of the intermediate synthesized supra (2.5 g, 8.6 mmol) and phosphorous pentoxide/methanesulfonyl chloride (1:10) (30 ml) was heated at 100° C. for about one hour. The reaction mixture was then stirred with ice as 5N sodium hydroxide was added to raise the pH to 14. This mixture was then partitioned with ethyl acetate in a separation funnel. The ethyl acetate layer was removed and the aqueous layer was washed with ethyl acetate (3×100 ml). The organic layers were combined and dried over potassium carbonate overnight. The solution was filtered and the solvent removed in vacuo to yield 2.2 grams (94.6%) of crude product.

The product was purified by chromatography using a hexanes/ethyl acetate (4:1) solution as the eluent to yield 1.98 grams (85.2%) of the pure title product. NMR, MS 271 (M$^+$), mp 108°–110° C.

Analysis for $C_{19}H_{14}N_2$: Theory: C, 84.42; H, 5.22; N, 10.36. Found: C, 84.72; H, 5.27; N, 10.35.

EXAMPLE 2

Synthesis of 1-phenyl-2-(4-methoxyphenyl)benzimidazole

A solution of N-phenyl-o-phenylenediamine (10 mmol, 1.84 g) in 100 ml diethyl ether was stirred at room temperature as p-anisoyl chloride {1 mmol, 1.71 g) was added dropwise. The resulting mixture was stirred at room temperature for about 96 hours. A precipitate formed before half of the anisoyl chloride/diethyl ether was added.

The resulting reaction mixture was partitioned with 1N sodium hydroxide and the organic layer separated. The aqueous layer was extracted with ethyl acetate (3×100 ml). The organic layers were combined and dried over potassium carbonate overnight, filtered, and the solvents were removed in vacuo. This yielded 3.57 grams of a dark brown crude product. Further purification could be performed by way of recrystallization from methylene chloride to yield a homogenous spot as determined by chromatography. mp 147°–149° C.

A solution of the intermediate prepared supra (3.19 g, 10 mmol) in 35 ml phosphorous pentoxide/methanesulfonyl chloride (1:10) was stirred at 100° C. for about 2.5 hours. The resulting reaction mixture was poured over ice and stirred as aqueous sodium hydroxide was added. The final solution had a pH of 14. This solution was partitioned with ethyl acetate. The ethyl acetate layer was removed and the aqueous layer was extracted with ethyl acetate (3×100 ml). The organic layers were combined and washed with saturated sodium chloride. This was then dried over potassium carbonate, filtered, concentrated in vacuo to yield a brown/dark red crude product.

This crude product was purified by chromatography using hexanes/ethyl acetate (9:1) as eluent to yield 1.38 grams of the title product. NMR, MS 301(M$^+$), mp 105°–107° C.

Analysis for $C_{20}H_{16}N_2O$: Theory: C, 79.98; H, 5.37; N, 9.33. Found: C, 79.77; H, 5.38; N, 9.11.

EXAMPLE 3

Synthesis of 1-phenyl-2-phenylmethylbenzimidazole

The title intermediate was synthesized in substantial accordance with Journal of Medicinal Chemistry, 18:319 (1975). A solution of N-phenyl-o-phenylenediamine (10 mmol, 1.84 g) and 2-ethoxy-1-ethoxycarbonyl-1,2-dihydroquinoline (12 mmol, 2.97 g) was stirred in methylene chloride (60 ml) at room temperature. Phenylacetic acid (10 mmol, 1.36 g) in methylene chloride (30 ml) was added via dropping funnel and stirred at room temperature over a drying tube overnight. The resulting reaction mixture was partitioned with 6N sodium hydroxide. The methylene chloride layer was removed and the aqueous layer was extracted with ethyl acetate (3×100). The organic fractions were combined, dried over potassium carbonate, filtered and the solvents were removed in vacuo to yield 5.28 grams of a dark red/brown crude product.

The crude product was recrystallized from ethyl acetate and then diethyl ether to yield a white crystalline product (1.77 g, 58.5%) of the title product. mp 108°–110° C.

A portion of the intermediate synthesized supra (1.35 g, 4.5 mmol) and 30 ml of phosphorous pentoxide/methane sulfonyl hydroxide (1:10) were stirred at 100° C. for about 6 hours. The resulting reaction mixture was poured over ice and neutralized with aqueous sodium hydroxide (to pH 14). The aqueous layer was partitioned with ethyl acetate and separated. The aqueous layer was extracted with ethyl acetate (4×200 ml). The organic layers were combined, dried over potassium carbonate, and filtered. The solvent was removed in vacuo and the crude dark red/brown product was purified by chromatography using hexanes/ethyl acetate (9:1) as the eluent. MS 285(M$^+$), mp 106°–108° C.

Analysis for $C_{20}H_{16}N_2O$: Theory: C, 84.48; H, 5.67; N, 9.85. Found: C, 84.75; H, 5.78; N, 9.93.

EXAMPLE 4

Synthesis of 1-phenyl-2-(3-chlorophenyl)benzimidazole

A solution of N-phenyl-o-phenylenediamine (1.84 g, 10 mmol) in diethyl ether (80 ml) was stirred at room temperature as 3-chlorobenzoylchloride (1.95 g, 11 mmol) in diethyl ether (30 ml) was added dropwise. Precipitate formed almost immediately after total addition of the 3-chlorobenzoylchloride. The resulting reaction mixture was stirred at room temperature for about 3 hours.

The reaction mixture was partitioned with aqueous sodium hydroxide. The organic layer was removed and the aqueous layer was extracted with ethyl acetate (3×120 ml). The organic layers were combined, dried over potassium carbonate, and filtered. The solvent was removed in vacuo to yield 3.5 grams of the desired intermediate.

Further purification could be performed using thin layer chromatography with hexanes/ethyl acetate (9:1) as the eluent. mp 133°–134° C., NMR.

A solution of the intermediate prepared supra (2.50 g, 7.7 mmol) and 40 ml phosphorous pentoxide/methane sulfonyl hydroxide (1:10) was stirred at 100° C. for about 16 hours. This reaction mixture was then poured over ice and alkalinized with 5N sodium hydroxide (until pH=14). This aqueous solution was then extracted with ethyl acetate (5×150 ml). The organic layers were combined and dried over potassium carbonate, filtered, and concentrated in vacuo to yield 2.2 grams of crude red/brown product.

This crude product was further purified by chromatography using a hexanes/ethyl acetate (9:1) solution as the eluent. MS 305, 307, mp 107°–109° C.

Analysis for $C_{19}H_{13}ClN_2$: Theory: C, 74.88; H, 4.30; N, 9.19. Found: C, 74.68; H, 4.47; N, 9.25.

EXAMPLE 5

Synthesis of 1-phenyl-2-(4-chlorophenyl)benzimidazole

A solution of N-phenyl-o-phenylenediamine (1.84 g, 10 mmol) in diethyl ether (80 ml) was stirred at room temperature as 4-chlorobenzoylchloride (1.95 g, 11 mmol) in diethyl ether (30 ml) was added dropwise. Precipitate formed almost immediately after total addition of the 4-chlorobenzoylchloride. After total addition of the 4-chlorobenzoylchloride, the resulting reaction mixture was stirred at room temperature for about 17 hours.

The reaction mixture was partitioned with 1N sodium hydroxide. The diethyl ether layer was removed and the aqueous layer extracted with ethyl acetate (4×150 ml). The organic layers were combined, dried over potassium carbonate, filtered, and concentrated in vacuo to yield 3.72 grams (>99%) of a dark red/brown solid. The crude product could be used as is or could be further purified. In the further purification the crude product was triturated in diethyl ether and filtered to yield an off-white solid. mp 169°–171° C.

A portion of the intermediate synthesized above (crude, 2.84 g) was stirred in phosphorous pentoxide/methanesulfonyl hydroxide (1:10, 40 ml) at 100° C. for about 16 hours. The reaction mixture was poured over ice and alkalinized with 5N sodium hydroxide (pH=14). The aqueous layer was extracted with ethyl acetate (5×150 ml). The combined organic fractions were dried over potassium carbonate, filtered, and concentrated in vacuo to yield 2.52 grams of crude title product. Further purification could be accomplished by chromatography to yield a solid yellow crystal. MS 305, 307, mp 139°–141° C.

Analysis for $C_{19}H_{13}ClN_2$: Theory: C, 74.88; H, 4.30; N, 9.19. Found: C, 74.97; H, 4.33; N, 9.21.

EXAMPLE 6

Synthesis of 1-phenyl-2-(3-methoxyphenyl)benzimidazole

The titled intermediate was prepared essentially as described in Journal of Medicinal Chemistry, 18:319 (1975). A solution of N-phenyl-o-phenylenediamine (1.84 g, 10 mmol) and m-methoxybenzoic acid (1.52 g, 10 mmol) was stirred at room temperature in methylene chloride (80 ml). N-ethoxycarbonyl-2-ethoxy-1,2-dihydroquinoline (2.97 g) was added dropwise and the reaction was refluxed for about 16 hours. Additional N-ethoxycarbonyl-2-ethoxy-1,2-dihydroquinoline was added and the reaction was refluxed for an additional 18 hours.

The reaction mixture was partitioned with 1N sodium hydroxide. The organic layer (pH~14) was extracted with ethyl acetate (3×150 ml). The combined organic fractions were dried over potassium carbonate, filtered and concentrated in vacuo. Crude red oil was purified by chromatography using hexanes/ethyl acetate (9:1) as the eluent. White solid crystallized out of several fractions. mp 118°–120° C.

A solution of the intermediate prepared above (1.08 g, 3.4 mmol) in chloroform (85 ml) was stirred at room temperature as phosphorous oxychloride (0.52 g, 3.4 mmol) in chloroform (35 ml) was added dropwise. The reaction mixture was then refluxed overnight.

The reaction mixture was partitioned with 1N sodium hydroxide. The organic layer was removed and the aqueous layer was extracted with chloroform (3×150 ml). The organic layers were combined, washed with a saturated sodium chloride solution, dried over potassium carbonate, filtered and the solvents were removed in vacuo to yield 1.18 grams (>99%).

The reaction product was further purified by chromatography using a hexanes/ethyl acetate (9:1) solution as eluent. MS 301($M^+$), mp 110°–111° C.

Analysis for $C_{20}H_{16}N_2O$: Theory: C, 79.98; H, 5.37; N, 9.33. Found: C, 79.72; H, 5.49; N, 9.39.

EXAMPLE 7

Synthesis of 1-phenyl-2-(4-nitrophenyl)benzimidazole 1-phenylamine-2-[(4-nitrophenyl)carbonylamino]benzene A solution of N-phenyl-o-phenylenediamine (1.84 g, 10 mmol) in diethyl ether (75 ml) was stirred at room temperature as 4-nitrobenzoylchloride (1.86 g, 10 mmol) in diethyl ether (40 ml) was added dropwise. A precipitate quickly formed. The reaction was stirred overnight.

The reaction mixture was partitioned with 1N sodium hydroxide and the organic layer removed. The aqueous layer (pH~14) was extracted with ethyl acetate (3×100 ml). The organic layers were combined, washed with saturated sodium chloride, dried over potassium carbonate, filtered and concentrated in vacuo.

The resulting crude product was triturated with diethyl ether and filtered to yield 2.48 grams of an orange/brown product was homogenous by chromatography. mp 169°–171° C.

A solution of the above-prepared intermediate (2.48 g, 7.4 mmol) in chloroform (80 ml) was stirred at room temperature as phosphorous oxychloride (1.13 g, 7.4 mmol) in chloroform (35 ml) was added dropwise. After constant addition the reaction mixture was refluxed overnight.

The reaction mixture was cooled and partitioned with 1N sodium hydroxide (pH~14). The organic layer was separated and the aqueous layer was extracted with chloroform (3×100 ml). The organic layers were combined, washed with saturated sodium chloride solution, dried over potassium carbonate, filtered, and the solvents were removed in vacuo to yield 2.50 grams of a yellow/green solid. The reaction product was purified by chromatography using a hexanes/ ethyl acetate (4:1) solution as eluent. MS 316($M^+$), mp 175°–177° C.

Analysis for $C_{19}H_{13}N_3O_2$: Theory: C, 72.37; H, 4.15; N, 13.33. Found: C, 72.67; H, 4.16; N, 13.30.

EXAMPLE 8

Synthesis of 1-(4-chlorophenyl)-2-phenylbenzimidazole

A solution of N-(4-chlorophenyl)-1,2-phenylenediamine (2.19 g, 10 mmol) in diethyl ether (75 ml) was stirred at room temperature as benzoyl chloride (1.41 g, 10 mmol) in diethyl ether (30 ml) was added dropwise. A precipitate quickly formed. The reaction mixture was stirred overnight and partitioned with 1N sodium hydroxide.

The organic layer was removed and the aqueous layer (pH~14) was extracted with ethyl acetate (3×150 ml). The organic layers were combined, washed with saturated sodium chloride, dried over potassium carbonate, filtered and removed in vacuo. The crude product was triturated in diethyl ether to yield 1.84 grams (57%) of a white solid which was chromatographically homogenous. mp 158°–160° C.

A solution of the intermediate prepared supra (0.33 g, 7.2 mmol) in chloroform (80 ml) was stirred at room temperature as phosphorous oxychloride (1.10 g, 7.2 mmol) in chloroform (30 ml) was added dropwise. After the addition was complete the reaction mixture was refluxed overnight. The reaction mixture was alkalinized to pH=14 with 1N sodium hydroxide and separated.

The aqueous layer was extracted with chloroform (3×10 ml). The organic layers were combined, washed with a saturated sodium chloride, dried over potassium carbonate, filtered, and the solvents were removed in vacuo to yield 2.45 grams of a red/brown oil which solidified upon setting at room temperature. The product was purified by chromatography using a hexanes/ethyl acetate (4:1) as eluent. MS 305, 307, mp 122°–123° C.

Analysis for $C_{19}H_{13}ClN_2$: Theory: C, 74.88; H, 4.30; N, 9.19. Found: C, 75.18; H, 4.30; N, 9.15.

EXAMPLE 9

Synthesis of 1-phenyl-2-(3-trifluoromethylphenyl)benzimidazole

A solution of N-phenyl-o-phenylenediamine (1.84 g, 10 mmol) in diethyl ether (80 ml) was stirred at room temperature as m-trifluorormethylbenzoyl chloride (2.09 g, 10 mmol) in diethyl ether (30 ml) was added dropwise. The reaction mixture was stirred overnight.

The reaction mixture was partitioned with 1N sodium hydroxide (pH~14) and the organic layer removed. The aqueous layer was extracted with ethyl acetate (3×100 ml). The organic layers were combined, washed with a saturated sodium chloride solution, dried over potassium carbonate, filtered, and the solvents were removed in vacuo to yield a dark red/brown oil which solidified upon standing at room temperature. The reaction product was purified by chromatography using a hexanes/ethyl acetate (4:1) solution as eluent.

A solution of the intermediate prepared above (3.20 g, 9.0 mmol) in chloroform (85 ml) was stirred at room temperature as phosphorous oxychloride (1.78 g, 9 mmol) in chloroform (35 ml) was added dropwise. The reaction mixture was refluxed overnight.

The reaction mixture was partitioned with 1N sodium hydroxide. The organic layer was removed and the aqueous layer was extracted with chloroform (3×150 ml). The organic layers were combined, washed with a saturated sodium chloride solution, dried over potassium carbonate, filtered, and the solvents were removed in vacuo to yield 3.00 grams of a yellow/brown oil which solidified upon standing.

The reaction product was further purified by chromatography using a hexanes/ethyl acetate 9:1 to 4:1) solution as eluent, yielding 1.89 grams (62%) of a light yellow solid. MS 339($M^+$), mp 99°–101° C.

Analysis for $C_{20}H_{13}F_3N_2$: Theory: C, 71.00; H, 3.87.; N, 8.28. Found: C, 71.21; H, 4.07; N, 8.42.

EXAMPLE 10

Synthesis of 1-phenyl-2-(3-nitrophenyl)benzimidazole

A solution of N-phenyl-o-phenylenediamine (1.84 g, 10 mmol) in diethyl ether (80 ml) was stirred at room temperature as 3-nitrobenzoyl chloride (1.86 g, 10 mmol) in diethyl ether (30 ml) was added dropwise. The reaction mixture was stirred overnight at room temperature.

The reaction mixture was partitioned with 1N sodium hydroxide. The organic layer was removed and the aqueous layer was extracted with ethyl acetate (3×100 ml). The organic layers were combined, washed with a saturated sodium chloride solution, dried over potassium carbonate, filtered, and the solvents were removed in vacuo.

The product was purified by trituration with diethyl ether to yield 2.19 g (65.7%) of a yellow solid. mp 127°–129° C.

A solution of the intermediate prepared above (2.9 g, 8.7 mmol) in chloroform (85 ml) was stirred at room temperature was phosphorous oxychloride (in 35 ml chloroform) was added dropwise. The reaction mixture was then refluxed overnight.

The reaction mixture was partitioned with 1N sodium hydroxide and the organic layer was removed. The aqueous layer was extracted with chloroform (3×120 ml). The organic fractions were combined, washed with a saturated sodium chloride solution, dried over potassium carbonate, filtered, and the solvents were removed in vacuo to yield 2.50 grams of a brown/green solid.

The reaction product was further purified using thin layer chromatography with a hexanes/ethyl acetate (9:1 to 4:1) solution as eluent. MS 316($M^+$), mp 166°–168° C.

Analysis for $C_{19}H_{13}N_3O_2$: Theory: C, 72.37; H, 4.16; N, 13.33. Found: C, 72.54; H, 4.27; N, 13.55.

EXAMPLE 11

Synthesis of 1-(4-chlorophenyl)-2-(4-chlorophenyl)benzimidazole

A solution of N-(4-chlorophenyl)-1,2-phenylenediamine (2.19 g, 10 mmol) in diethyl ether (85 ml) was stirred at room temperature as 4-chlorobenzoyl chloride (1.75 g, 10 mmol) in diethyl ether (35 ml) was added dropwise. The reaction mixture was stirred overnight at room temperature.

The reaction mixture was partitioned with 1N sodium hydroxide. The organic layer was removed and the aqueous layer (pH~14) was extracted with ethyl acetate (3×100 ml). The organic fractions were combined, washed with a saturated sodium chloride solution, dried over potassium carbonate, filtered, and the solvents were removed in vacuo to yield a crude red/brown solid.

The reaction product was purified by trituration with diethyl ether to yield 2.91 grams (81.5%) of an off-white solid which was chromatographically homogeneous. mp 180°–181° C.

A solution of the intermediate prepared above (3.16 g, 8.8 mmol) in chloroform (90 ml) was stirred at room temperature as phosphorous oxychloride (1.36 g, 8.8 mmol) in chloroform (35 ml) was added dropwise. The reaction mixture was then refluxed overnight.

The mixture was partitioned with 1N sodium hydroxide and the organic layer was removed. The aqueous fraction was extracted with chloroform (3×150 ml). The organic layers were combined, washed with a saturated sodium chloride solution, dried over potassium carbonate, filtered, and the solvents were removed in vacuo to yield 2.83 grams of a gray/brown solid.

The reaction product was further purified by chromatography to yield 2.31 grams (77%) of a light pink solid. MS 339, 341, mp 162°–164° C.

Analysis for $C_{19}H_{12}Cl_2N_2$: Theory: C, 67.27; H, 3.57; N, 8.30. Found: C, 67.45; H, 3.72; N, 8.36.

EXAMPLE 12

Synthesis of 1-phenyl-2-(4-trifluoromethylphenyl)benzimidazole

A solution of N-phenyl-o-phenylenediamine (1.84 g, 10 mmol) in diethyl ether (85 ml) was stirred at room temperature as 4-(trifluoromethyl)benzoyl chloride (2.09 g, 10 mmol) in diethyl ether (30 ml) was added dropwise. The reaction mixture was stirred overnight at room temperature.

The reaction mixture was partitioned with 1N sodium hydroxide. The organic layer was removed and the aqueous layer extracted with ethyl acetate (3×100 ml). The organic layers were combined, washed with a sodium chloride solution, dried over potassium carbonate, filtered, and the solvents were removed in vacuo to yield a brown/black solid.

The crude product was triturated with diethyl ether and vacuum filtered to yield 2.56 grams (72%) of a yellow solid which was homogeneous on thin layer chromatography. mp 143°–145° C.

A solution of the intermediate prepared above (3.25 g, 9.1 mmol) in chloroform (85 ml) was stirred at room temperature as phosphorous oxychloride in chloroform (35 ml) was added dropwise. The reaction mixture was partitioned with 1N sodium hydroxide.

The organic layer was removed and the aqueous layer was extracted with chloroform (3×150 ml). The organic layers were combined, washed with a saturated sodium chloride solution, dried over potassium carbonate, filtered, and the solvents were removed in vacuo to yield a red/brown oil which solidified upon standing.

The reaction product was further purified by chromatography using a hexanes/ethyl acetate (9:1 to 4:1) solution as eluent. Yield: 2.39 grams (77.6%) of a light yellow solid. MS 339(M⁺), mp 133°–135° C.

Analysis for $C_{20}H_{13}F_3N_2$: Theory: C, 71.00; H, 3.87; N, 8.28. Found: C, 71.28; H, 3.99; N, 8.46.

EXAMPLE 13

Synthesis of 1-phenyl-2-(2-naphthyl)benzimidazole

A solution of N-phenyl-o-phenylenediamine (1.84 g, 10 mmol) was stirred at room temperature in diethyl ether (85 ml) as naphthoyl chloride (10 mmol, 1.91 g) in diethyl ether (35 ml) was added dropwise. The reaction mixture was stirred overnight at room temperature.

The reaction mixture was alkalinized with 1N sodium hydroxide. The organic layer was removed. The aqueous layer (pH~14) was extracted with ethyl acetate (3×100 ml). The organic fractions were combined, washed with a saturated sodium chloride solution, dried over potassium carbonate, filtered, and the solvents were removed in vacuo to yield a red/brown solid (3.91 g, >99%).

The solid was triturated with diethyl ether and the remaining solid was collected by vacuum filtration. The reaction product was further purified by chromatography using a hexanes/ethyl acetate (9:1) solution as eluent. mp 147°–149° C.

A solution of the intermediate prepared above (2.4 g, 7.1 mmol) in chloroform (85 ml) was stirred at room temperature as phosphorous oxychloride (1.1 g, 7.1 mmol) in chloroform (35 ml) was added dropwise. After the addition the reaction mixture was refluxed overnight.

The reaction mixture was alkalinized with 1N sodium hydroxide. The organic layer was removed and the aqueous layer was extracted with chloroform (3×150 ml). The organic layers were combined, washed with a saturated sodium chloride solution, dried over potassium carbonate, filtered, and the solvents were removed in vacuo to yield 2.38 grams (>99%) of a brown solid.

The reaction product was further purified by chromatography using a hexanes/ethyl acetate solution as the eluent to yield 1.91 grams (84%) of a light yellow solid. MS 321(M⁺), mp 169°–170° C.

Analysis for $C_{23}H_{16}N_2$: Theory: C, 86.22; H, 5.03; N, 8.04. Found: C, 86.21; H, 5.24; N, 8.61.

EXAMPLE 14

Synthesis of 1-phenyl-2-(3,5-dimethoxyphenyl)benzimidazole

A solution of N-phenyl-o-phenylenediamine (1.84 g, 10 mmol) in diethyl ether (85 ml) was stirred at room temperature as 3,5-dimethylbenzoyl chloride (2.00 g, 1.84 mmol) in diethyl ether (35 ml) was added dropwise. The reaction mixture was stirred at room temperature overnight.

The reaction mixture was alkalinized with 1N sodium hydroxide and the organic layer was removed. The aqueous layer was extracted with ethyl acetate (3×100 ml). The organic layers were combined, washed with a saturated sodium chloride solution, dried over potassium carbonate, filtered, and the solvents were removed in vacuo to yield 3.46 grams of a red/brown oil which solidified upon standing.

Further purification of the title intermediate was achieved by chromatography. mp 107°–109° C.

A solution of the crude product of the reaction above (2.3 g, 6.6 mmol) in chloroform (85 ml) was stirred at room temperature as phosphorous oxychloride (1.01 g, 6.6 mmol) in chloroform (25 ml) was added dropwise. The reaction mixture was then refluxed overnight.

The reaction mixture was alkalinized with 1N sodium hydroxide. The organic layer was removed and the aqueous layer was extracted with methylene chloride (3×100 ml). The organic layers were combined, washed with saturated sodium chloride solution, dried over potassium carbonate, filtered, and the solvents were removed in vacuo to yield a red/brown oil which solidified upon standing.

Further purification of the reaction product was accomplished by chromatography, employing a hexanes/ethyl acetate mixture as the eluent to yield 1.91 grams (87.6%) of a light yellow solid. MS 331(M⁺), mp 98°–99° C.

Analysis for $C_{21}H_{18}N_2O_2$: Theory: C, 76.34; H, 5.49; N, 8.48. Found: C, 76.17; H, 5.60; N, 8.51.

EXAMPLE 15

Synthesis of 1-phenyl-2-(3,4-dimethoxyphenyl)benzimidazole

A solution of N-phenyl-o-phenylenediamine (1.84 g, 10 mmol) in diethyl ether (85 ml) was stirred at room temperature as 3,4-dimethoxybenzoyl chloride (2.01 g, 10 mmol) in 40 ml of diethyl ether was added dropwise. The reaction mixture was then stirred overnight at room temperature.

The reaction mixture was then alkalinized with 1N sodium hydroxide. The organic layer was removed and the aqueous layer was extracted with diethyl ether (3×150 ml). The organic fractions were combined, washed with a saturated sodium chloride solution, dried over potassium carbonate, filtered, and the solvents were removed in vacuo to yield 3.11 grams.

This intermediate was further purified by chromatography using a hexanes/ethyl acetate solution as the eluent, followed by trituration with hexanes to yield a white crystalline solid. mp 159°–160° C.

A solution of the intermediate prepared supra (3.11 g, 8.9 mmol) in chloroform (30 ml) was stirred at room temperature as phosphorous oxychloride (1.40 g, 9 mmol) in chloroform (30 ml) was added dropwise. The reaction mixture was then refluxed overnight. The reaction mixture was partitioned with 1N sodium hydroxide.

The organic fraction was removed and the aqueous phase was extracted with methylene chloride (3×150 ml). The organic fractions were combined, washed with saturated sodium chloride solution, dried over potassium carbonate, filtered, and the solvents were removed in vacuo to yield a brown oil which solidified upon standing.

The crude product was partitioned between 1N hydrochloric acid and a hexanes/ethyl acetate (1:1) solution. The aqueous layer was removed and the organic layer was extracted with 1N hydrochloric acid (3×100 ml). The aqueous fractions were combined and alkalinized to pH 14 with sodium hydroxide. This basified solution was extracted with ethyl acetate (5×100 ml). The organic layers were combined, washed with a saturated sodium chloride solution, dried over potassium carbonate, filtered, and the solvents were removed in vacuo to yield 1.70 grams (57.8%) of a pink solid. MS 331(M$^+$), mp 114°–115° C.

Analysis for $C_{21}H_{18}N_2O_2$: Theory: C, 76.34; H, 5.49; N, 8.48. Found: C, 76.31; H, 5.63; N, 8.53.

EXAMPLE 16

Synthesis of 1-phenyl-2-(3,4,5-trimethoxyphenyl)benzimidazole

A solution of N-phenyl-o-phenylenediamine (1.84 g, 10 mmol) in diethyl ether (90 ml) was stirred at room temperature as 3,4,5-trimethoxybenzoyl chloride (2.31 g, 10 mmol) in diethyl ether (40 ml) was added dropwise. The reaction mixture was then stirred overnight at room temperature. The solvents were then removed in vacuo leaving N-[(3,4,5-trimethoxyphenyl)carbonyl]-N'-phenylphenylenediamine.

The crude intermediate (3.6 g, 9.5 mmol) in chloroform (100 ml) was stirred at room temperature as phosphorous oxychloride (1.5 g, 9.5 mmol) in chloroform (20 ml) was added dropwise. The reaction mixture was then stirred at room temperature for about 72 hours.

The reaction mixture was partitioned between 1N hydrochloric acid and ethyl acetate. The organic phase was discarded and the aqueous phase was alkalinized with 1N sodium hydroxide. The aqueous solution was then extracted with ethyl acetate (3×100 ml). The organic fractions were combined and dried over potassium carbonate. The solvents were removed in vacuo to yield the title product as a white solid (2.08 g, 61%). MS 361(M$^+$), mp 139°–141° C.

Analysis for $C_{22}H_{20}N_2O_3$: Theory: C, 73.32; H, 5.59; N, 7.77. Found: C, 73.17; H, 5.71; N, 7.72.

EXAMPLE 17

Synthesis of 1-(4-chlorophenyl)-2-(4-methoxyphenyl)benzimidazole

A solution of N-(4-chlorophenyl)-1,2-phenylenediamine (2.13 g, 10 mmol) in diethyl ether (90 ml) was stirred at room temperature as p-anisoyl chloride (1.71 g, 10 mmol) in diethyl ether (45 ml) was added dropwise. The mixture was stirred overnight at room temperature.

The reaction mixture was partitioned with 1N sodium hydroxide. The orgnaic layer was removed and the aqueous fraction was extracted with ethyl acetate (3×150 ml). The organic layers were combined, washed with a saturated sodium chloride solution, dried over potassium carbonate, filtered, and the solvents were removed in vacuo to yield 3.6 grams of a brown/pink solid.

The desired intermediate was further purified by chromatography using a hexanes/ethyl acetate (3:1) solution as the eluent to yield a light pink solid. mp 162°–164° C.

The intermediate prepared above (3.40 grams, 9.6 mmol) was dissolved in chloroform (90 ml). This solution was stirred at room temperature as phosphorous oxychloride in chloroform (40 ml) was added dropwise. The reaction mixture was refluxed overnight.

The reaction mixture was partitioned with 1N sodium hydroxide and the organic layer removed. The aqueous fraction was further extracted with methylene chloride (3×150 ml). The organic layers were combined, washed with a saturated sodium chloride solution, dried over potassium carbonate, filtered, and the solvents were removed in vacuo.

The reaction product was further purified by chromatography to yield 2.64 grams (82.1%) of a light pink solid. MS 335, 337, mp 183°–185° C.

Analysis for $C_{20}H_{15}ClN_2O$: Theory: C, 71.75; H, 4.52; N, 8.37. Found: C, 71.67; H, 4.77; N, 8.59.

EXAMPLE 18

Synthesis of 1-phenyl-2-(4-methylphenyl)benzimidazole

A solution of N-phenyl-o-phenylenediamine (1.84 g, 10 mmol) in diethyl ether (85 ml) was stirred at room temperature as p-toluoyl chloride (1.60 g, 10 mmol) in diethyl ether (35 ml) was added dropwise. The reaction mixture was stirred overnight at room temperature.

The reaction mixture was alkalinized with 1N sodium hydroxide. The organic layer was removed and the aqueous fraction was extracted with ethyl acetate (3×150 ml). The organic layers were combined, washed with a saturated sodium chloride solution, dried over potassium carbonate, filtered, and the solvents were removed in vacuo to yield 3.18 grams of a red/brown solid.

The intermediate was further purified by chromatography using a hexanes/ethyl acetate (9:1) solution as the eluent to yield a yellow solid. mp 143°–145° C.

The intermediate prepared above (2.63 g, 8.6 mmol) was dissolved in chloroform (85 ml). This solution was stirred at room temperature as phosphorous oxychloride (1.35 g, 8.6 mmol) in chloroform (30 ml) was added dropwise. The reaction mixture was refluxed overnight.

The reaction mixture was partitioned with 1N sodium hydroxide and the organic layer removed. The aqueous layer was extracted with methylene chloride (3×150 ml). The organic fractions were combined, washed with a saturated sodium chloride solution, dried over potassium carbonate, filtered and the solvents were removed in vacuo to yield a red/brown oil which solidified upon standing.

The reaction product was further purified by chromatography using a hexanes/ethyl acetate (4:1) solution as the eluent. The fractions were combined, the solvents removed in vacuo and the resulting oil was triturated with diethyl ether. The title product was recystallized from diethyl ether/hexanes to yield 1.54 grams (63%). MS 285(M$^+$)

Analysis for $C_{20}H_{16}N_2$: Theory: C, 84.48; H, 5.67; N, 9.85. Found: C, 85.60; H, 5.94; N, 10.45.

EXAMPLE 19

Synthesis of 1-phenyl-2-(3-methylphenyl)benzimidazole

A solution of N-phenyl-o-phenylenediamine (1.84 g, 10 mmol) in diethyl ether (90 ml) was stirred at room temperature as m-toluoyl chloride (1.55, 10 mmol) in diethyl ether (30 ml) was added dropwise. The reaction mixture was stirred at room temperature overnight.

The reaction mixture was then alkalinized with 1N sodium hydroxide. The organic layer was removed and the aqueous fraction was extracted with ethyl acetate (3×150 ml). The organic fractions were combined, washed with a saturated sodium chloride solution, dried over potassium carbonate, filtered, and the solvents were removed in vacuo to yield 3.12 grams of a gray/brown solid.

The intermediate was further purified by chromatography. mp 129°–130° C.

The intermediate prepared above (2.5 g, 8.3 mmol) in chloroform (95 ml) was stirred at room temperature as phosphorous oxychloride (1.30 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (4:1) solution as eluent. The product was recrystallized from hexanes to yield 0.97 grams (41.1%) of a white solid. MS 285(M$^+$), mp 69°–71° C.

Analysis for $C_{20}H_{16}N_2$: Theory: C, 84.48; H, 5.67; N, 9.85. Found: C, 84.48; H, 5.72; N, 9.80.

EXAMPLE 20

Synthesis of 1-phenyl-2-(4-cyanophenyl)benzimidazole

A solution of N-phenyl-o-phenylenediamine (1.84 g, 10 mmol) in diethyl ether (100 ml) was stirred at room temperature as 4-cyanobenzoyl chloride (1.66 g, 10 mmol) in diethyl ether (40 ml) was added dropwise. The reaction mixture was stirred overnight at room temperature.

The reaction mixture was partitioned with 1N sodium hydroxide. The organic fraction was removed and the aqueous layer was extracted with ethyl acetate (3×150 ml). The combined organic layers were washed with a saturated sodium chloride solution, dried over potassium carbonate, filtered and the solvents were removed in vacuo to yield 3.31 grams of a red/black oily gum.

This oily gum (2.8 g, 8.9 mmol) was dissolved in chloroform (90 ml). This solution was stirred as phosphorous oxychloride (1.40 g, 9.0 mmol) in chloroform (35 ml) was added dropwise. This reaction mixture was refluxed overnight.

The reaction mixture was alkalinized with 1N sodium hydroxide. The organic layer was removed and the aqueous fraction was extracted with methylene chloride (3×150 ml). The organic layers were combined, washed with a saturated sodium chloride solution, dried over potassium carbonate, filtered, and the solvents were removed in vacuo to yield a red/brown oil.

The reaction product was further purified by chromatography using a hexanes/ethyl acetate solution as eluent. The title product then was recystallized from ethyl acetate to yield a white solid. MS 296(M$^+$), mp 182°–184° C.

Analysis for $C_{20}H_{13}N_3$: Theory: C, 81.34; H, 4.44; N, 14.23. Found: C, 81.55; H, 4.50; N, 14.47.

EXAMPLE 21

Synthesis of 1-phenyl-2-cyclohexylbenzimidazole

A solution of N-phenyl-o-phenylenediamine (1.84 g, 10 mmol) in diethyl ether (85 ml) was stirred at room temperature as cyclohexanecarbonyl chloride (1.46 grams, 10 mmol) in diethyl ether (3 ml) was added dropwise. The reaction mixture was stirred at room temperature overnight.

The reaction mixture was alkalinized with 1N sodium hydroxide. The organic fraction was removed and the aqueous phase was extracted with ethyl acetate (3×150 ml). The organic fractions were combined, washed with saturated sodium chloride solution, dried over potassium carbonate, filtered, and the solvents were removed in vacuo to yield 2.81 grams of a brown solid. The reaction product was further purified by chromatography to yield N-phenyl-N'-cyclohexylcarbonyl-phenylenediamine as a yellow solid.

The intermediate prepared above (2.0 g, 7 mmol) was dissolved in chloroform (80 ml). This solution was stirred at room temperature as phosphorous oxychloride (1.05 g, 7 mmol) in chloroform (30 ml) was added dropwise. The reaction mixture was refluxed overnight.

The reaction mixture was alkalinized with 1N sodium hydroxide. The organic layer was removed and the aqueous layer was extracted with methylene chloride (3×150 ml). The organic fractions were combined, washed with a saturated sodium chloride solution, dried over potassium carbonate, filtered, and the solvents were removed in vacuo to yield 2.81 grams of a black/red oil which solidified upon standing.

The reaction product was further purified by partitioning between 1N hydrochloric acid and an ethyl acetate/hexanes (1:1) solution. The aqueous layer was alkalinized to pH 10 using 1N sodium hydroxide. The aqueous fraction was then extracted with ethyl acetate (4×250 ml). The organic layers were combined, washed with a saturated sodium chloride solution, dried over potassium carbonate, filtered and the solvents were removed in vacuo to yield 1.47 grams (76%) of a light yellow solid. MS 277 (M$^+$), mp 99°–101° C.

Analysis for $C_{19}H_{20}N_2$: Theory: C, 82.57; H, 7.29; N, 10.14. Found: C, 82.33; H, 7.45; N, 10.21.

EXAMPLE 22

Synthesis of 1-phenyl-2-(2-chlorophenyl)benzimidazole

A solution of N-phenyl-o-phenylenediamine (1.84 g, 10 mmol) in diethyl ether (85 ml) was stirred at room temperature as 2-chlorobenzoyl chloride (1.76 g, 10 mmol) in diethyl ether (35 ml) was added dropwise. The reaction mixture was stirred overnight at room temperature.

The reaction mixture was alkalinized with 1N sodium hydroxide and the organic layer removed. The aqueous phase was extrated with ethyl acetate (3×100 ml). The organic fractions were combined, washed with a saturated sodium chloride solution, dried over potassium carbonate, filtered, and the solvents were removed in vacuo to yield 3.2 grams (>99%) of a gray/brown solid.

The crude product prepared supra (2.7 g, 8.4 mmol) was dissolved in chloroform (95 ml). This solution was stirred at room temperature as phosphorous oxychloride (1.3 g, 8.5 mmol) in chloroform (30 ml) was added dropwise. The reaction mixture was refluxed overnight and then partitioned with 1N sodium hydroxide.

The organic layer was removed and the aqueous phase was extracted with methylene chloride (3×150 ml). The combined organic layers were washed with a saturated sodium chloride solution, dried over potassium carbonate, filtered, and the solvents were removed in vacuo.

The crude product was further purified by chromatography using a hexanes/ethyl acetate (9:1) solution as the eluent. The recovered product was triturated in hexanes and filtered to yield 1.31 grams (51.2%) of a light yellow solid. MS 305, 307, mp 146°–148° C.

Analysis for $C_{19}H_{13}C_1N_2$: Theory: C, 74.88; H, 4.30; N, 9.19. Found: C, 75.16; H, 4.31; N, 9.21.

EXAMPLE 23

Synthesis of 1-phenyl-2-(2-methylphenyl)benzimidazole

A solution of N-phenyl-o-phenylenediamine (1.84 g, 10 mmol) in diethyl ether (90 ml) was stirred at room temperature as o-toluoyl chloride (1.55 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (3:1) solution as the eluent. Trituration with hexanes and subsequent filtration yielded a white solid. mp 118°–120° C.

The intermediate prepared above (2.52 g, 8.3 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (9:1 to 4:1) solution as the eluent to yield a pale yellow oil. The product was triturated with hexanes to yield a light yellow solid. MS 285($M^+$), mp 99°–101° C.

Analysis for $C_{20}H_{16}N_2$: Theory: C, 84.48; H, 5.67; N, 9.85. Found: C, 84.48; H, 5.72; N, 9.80.

EXAMPLE 24

Synthesis of 1-phenyl-2-(2-methoxyphenyl)benzimidazole

A solution of N-phenyl-o-phenylenediamine (1.84 g, 10 mmol) in diethyl ether (90 ml) was stirred at room temperature as 2-methoxybenzoyl chloride (1.55 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (9:1) solution as eluent. The reaction product was recrystallized from hexanes. mp 178°–180° C.

The intermediate prepared above (2.65 g, 8.3 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (4:1) solution as eluent to yield 1.64 grams (65.7%) of the title product as a white solid. MS 301($M^+$), mp 159°–160° C.

Analysis for $C_{20}H_{16}N_2O$: Theory: C, 79.98; H, 5.37; N, 9.33. Found: C, 80.01; H, 5.36; N, 9.40.

EXAMPLE 25

Synthesis of 1-phenyl-2-(3-cyanophenyl)benzimidazole

A solution of N-phenyl-o-phenylenediamine (1.84 g, 10 mmol) in diethyl ether (90 ml) was stirred at room temperature as 3-cyanobenzoyl chloride (1.66 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (4:1) solution as the eluent. The product was recrystallized from hexanes to yield a white solid. mp 141°–143° C.

The intermediate prepared above (2.63 g, 8.3 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (9:1 to 4:1) solution as eluent. The title product was recrystallized from hexanes and ethyl acetate. MS 296($M^+$), mp 153°–154° C.

Analysis for $C_{20}H_{13}N_3$: Theory: C, 81.34; H, 4.44; N, 14.23. Found: C, 81.60; H, 4.45; N, 14.38.

EXAMPLE 26

Synthesis of 1-dimethylaminoethyl-2-phenylbenzimidazole dihydrochloride

A solution of 2-phenylbenzimidazole (0.97 g, 5 mmol) in N,N-dimethylformamide (anhydrous, 20 ml) was stirred at room temperature under nitrogen atmosphere. Two equivalents of sodium hydride in 60% dispersion (0.40 g, 10 mmol) was quickly added and the reaction mixture was allowed to stir under nitrogen. N,N-Dimethylaminoethyl bromide hydrobromide (1.16 g, 5 mmol) in anhydrous N,N-dimethylformamide (12 ml) was added dropwise by syringe to the stirring mixture. The reaction mixture was stirred overnight at room temperature.

The reaction mixture was partitioned between acetic acid and ethyl acetate. The organic layer was discarded and the aqueous phase was extracted with diethyl ether (5×75 ml). All organic fractions were discarded.

The aqueous phase was alkalinized with 2N sodium hydroxide. This solution was then extracted with diethyl ether (4×100 ml). The organic fractions were combined, washed with a saturated sodium chloride solution, dried over potassium carbonate, filtered, and the solvents were removed in vacuo to yield 1.11 grams of a cloudy oil.

The crude product was stirred with 2N hydrochloric acid in ethanol. The solvents were removed in vacuo to yield 1.16 (66.8%) grams of the title product as a white solid. MS 309, mp 228°–231° C.

Analysis for $C_{17}H_{19}N_3 \cdot 2$ HCl: Theory: C, 60.36; H, 6.26; N, 12.42. Found: C, 60.09; H, 6.22; N, 12.18.

EXAMPLE 27

Synthesis of 1-phenyl-2-(3,4-dichlorophenyl)benzimidazole

A solution of N-phenyl-o-phenylenediamine (1.84 g, 10 mmol) in diethyl ether (90 ml) was stirred at room temperature as 3,4-dichlorobenzoyl chloride (2.10 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (4:1) solution as the eluent. The product was recrystallized from hexanes to yield a white solid. mp 146°–147° C.

The intermediate prepared above (3.00 g, 8.4 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (4:1) solution as eluent. The title product was recrystallized from hexanes and ethyl acetate as a white solid. MS 339, 341, mp 144°–146° C.

Analysis for $C_{19}H_{12}Cl_2N_2$: Theory: C, 67.27; H, 3.57; N, 8.26. Found: C, 67.53; H, 3.61; N, 8.13.

EXAMPLE 28

Synthesis of 1-(piperidin-1-ylethyl)-2-phenylbenzimidazole dihydrochloride

A solution of 2-phenylbenzimidazole (0.97 g, 5 mmol) in N,N-dimethylformamide (anhydrous, 20 ml) was stirred at room temperature under nitrogen atmosphere. Two equivalents of sodium hydride in 60% dispersion (0.40 g, 10 mmol) was quickly added and the reaction mixture was allowed to stir under nitrogen. N-(2-chloroethyl)piperidinyl (10 mmol) in anhydrous N,N-dimethylformamide (12 ml) was added dropwise by syringe to the stirring mixture. The reaction mixture was stirred overnight at room temperature.

The reaction mixture was partitioned between acetic acid and ethyl acetate. The organic layer was discarded and the aqueous phase was extracted with diethyl ether (5×75 ml). All organic fractions were discarded.

The aqueous phase was alkalinized with 2N sodium hydroxide. This solution was then extracted with diethyl ether (4×100 ml). The organic fractions were combined, washed with a saturated sodium chloride solution, dried over potassium carbonate, filtered, and the solvents were removed in vacuo to yield 1.11 grams of a cloudy oil.

This was then stirred in 2N hydrochloric acid in ethanol. The solvents were removed in vacuo, yielding the crude product, which was recrystallized twice from an ethyl acetate/ethanol solution. The solvents were removed in vacuo to yield 0.95 grams (50.2%) of the title product as a white solid. MS 306

Analysis for $C_{20}H_{23}N_3 \cdot 2$ HCl: Theory: C, 63.49; H, 6.66; N, 11.11. Found: C, 63.33; H, 6.64; N, 10.92.

EXAMPLE 29

Synthesis of 1-phenyl-2-(4-hydroxyphenyl)benzimidazole

A solution of 1-phenyl-2-(4-methoxyphenyl)benzimidazole (0.60 g, 2.0 mmol) in hydrobromic acid (6 ml) and acetic acid (6 ml) was refluxed for 40 hours. The reaction mixture was extracted with diethyl ether (5×150 ml) at a pH of 3–5. The organic solvents were discarded. The aqueous phase was alkalinized to pH 8–9 and extracted with ethyl acetate (5×150 ml). The organic fractions were combined and dried over potassium carbonate, then filtered and the solvents were removed in vacuo to yield a white solid. The solid was triturated in diethyl ether and filtered to yield 0.25 grams of the desired product.

Analysis for $C_{19}H_{14}N_2O \cdot 0.5$ $H_2O$: Theory: C, 77.27; H, 5.12; N, 9.48. Found: C, 77.56; H, 4.96; N, 9.39.

EXAMPLE 30

Synthesis of 1-phenyl-2-(3-nitro-4-chlorophenyl)benzimidazole

A solution of N-phenyl-o-phenylenediamine (1.84 g, 10 mmol) and 4-chloro-3-nitro-benzoic acid (2.07 g, 10 mmol) in anhydrous tetrahydrofuran was stirred at room temperature as N-ethoxycarbonyl-2-ethoxy-1,2-dihydroquinoline (3.71 g, 15 mmol) in tetrahydrofuran was added dropwise. The reaction was stirred at room temperature for about 72 hours.

The reaction mixture was alkalinized with 1N sodium hydroxide. The aqueous layer was extracted with ethyl acetate (4×100 ml). The organic fractions were combined, dried over potassium carbonate, filtered, and the solvents removed in vacuo to yield the crude product.

The reaction product was further purified by chromatography using a hexanes/ethyl acetate (4:1) solution as eluent.

The intermediate prepared above (3.00 g, 8.4 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (9:1) solution as eluent. The title product was recrystallized from fractions with ethyl acetate as a white solid. MS 349, 351, mp 179°–182° C.

Analysis for $C_{19}H_{12}ClN_3O_2$: Theory: C, 65.24; H, 3.46; N, 12.01. Found: C, 65.50; H, 3.51; N, 12.06.

EXAMPLE 31

Synthesis of 1-[2-(morpholin-4-yl)ethyl]-2-phenylbenzimidazole dihydrochloride

A solution of 2-phenylbenzimidazole (0.97 g, 5 mmol) in N,N-dimethylformamide (anhydrous, 20 ml) was stirred at 60° C. under nitrogen atmosphere. Two equivalents of sodium hydride in 60% dispersion (0.40 g, 10 mmol) was quickly added and the reaction mixture was allowed to stir under nitrogen. N-(2-chloroethyl)morpholine (0.93 g, 5 mmol) in anhydrous N,N-dimethylformamide (12 ml) was added dropwise by syringe to the stirring mixture. The reaction mixture was stirred overnight at 60° C.

The reaction mixture was partitioned between acetic acid and ethyl acetate. The organic layer was discarded and the aqueous phase was extracted with diethyl ether (5×75 ml). All organic fractions were discarded.

The aqueous phase was alkalinized with 2N sodium hydroxide. This solution was then extracted with diethyl ether (4×100 ml). The organic fractions were combined, washed with a saturated sodium chloride solution, dried over potassium carbonate, filtered, and the solvents were removed in vacuo to yield a cloudy oil.

The crude product was mixed with a 2N hydrochloric acid/ethanol (1:1) solution. The solvents were removed in vacuo to yield 1.52 grams (40%) of a white solid. MS 308.

Analysis for $C_{19}H_{21}N_3O \cdot 2$ HCl·EtOH: Theory: C, 59.16; H, 6.86; N, 9.85. Found: C, 59.20; H, 6.85; N, 9.89.

EXAMPLE 32

Synthesis of 1-phenyl-2-propylbenzimidazole

A solution of N-phenyl-o-phenylenediamine (1.84 g, 10 mmol) in tetrahydrofuran (90 ml) was stirred at room temperature under a nitrogen atmosphere as butanoyl chloride (1.28 g, 12 mmol) in tetrahydrofuran (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (3:1) solution as the eluent. The product was recrystallized from hexanes to yield a white solid.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (3:1) solution as eluent. The title product was recrystallized from hexanes and ethyl acetate as a white solid, yielding 1.55 grams (66%). MS 237, mp 53°–55° C.

Analysis for $C_{16}H_{16}N_2$: Theory: C, 81.32; H, 6.82; N, 11.85. Found: C, 81.06; H, 6.69; N, 12.02.

EXAMPLE 33

Synthesis of 1-phenyl-2-(thien-2-yl)benzimidazole

A solution of N-phenyl-o-phenylenediamine (1.84 g, 10 mmol) in diethyl ether (90 ml) was stirred at room temperature under a nitrogen atmosphere as an equimolar amount of 2-chlorocarbonylthiophene in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo to yield a red/brown oil.

The reaction product was further purified by trituration in diethyl ether. Recrystallization from ethyl acetate yielded a white solid which was homogeneous on thin layer chromatography. mp 150°–152° C.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (3:1) solution as eluent. The title product was recrystallized from hexanes and ethyl acetate as clear crystals. The solvent was removed in vacuo, yielding 1.70 grams (64%). MS 277, mp 118°–120° C.

Analysis for $C_{17}H_{12}N_2S$: Theory: C, 73.62; H, 4.72; N, 10.10. Found: C, 73.84; H, 4.48; N, 10.30.

EXAMPLE 34

Synthesis of 1-phenyl-2-(3-hydroxyphenyl)benzimidazole

A solution of 1-phenyl-2-(3-methoxyphenyl)benzimidazole (0.20 g, 0.67 mmol) and hydrobromic acid (4 ml) and acetic acid (4 ml) was refluxed for 48 hours. The reaction mixture was cooled and extracted with diethyl ether (5×150 ml) at pH 3–5. The organic fractions were discarded. The aqueous phase was alkalinized to pH 8–9 and extracted with ethyl acetate (5×150 ml). The organic layers were combined, washed with a saturated sodium chloride solution, dried over magnesium sulfate, filtered, and the solvents were removed in vacuo to yield a white solid. The solid was triturated with an ethyl acetate/diethyl ether mixture.

The reaction product was further purified by chromatography to yield 0.17 grams (88.6%) of a white solid. MS 287(M+), mp 245°–247° C.

Analysis for $C_{19}H_{14}N_2O \cdot 2$ $H_2O$: Theory: C, 78.71; H, 5.01; N, 9.66. Found: C, 78.79; H, 5.16; N, 9.70.

EXAMPLE 35

Synthesis of 1-phenyl-2-pentylbenzimidazole hydrochloride

A solution of N-phenyl-o-phenylenediamine (1.84 g, 10 mmol) in diethyl ether (90 ml) was stirred at room temperature as an equimolar amount of hexanoyl chloride in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo to yield a red/brown oil.

The reaction product was further purified by trituration in diethyl ether. Recrystallization from ethyl acetate yielded a white solid which was homogeneous on thin layer chromatography.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo to yield a red/brown oil.

The reaction product was further purified by chromatography using a hexanes/ethyl acetate (3:1) solution as eluent to yield 1.82 grams (69.2%) as a red oil. The red oil was stirred in a 2N hydrochloric acid/ethanol (1:1) solution for ten minutes. The ethaol was removed in vacuo to yield 2.1 grams of a brown/green solid. The title product was recrystallized from an ethyl acetate/ethanol (1:1) solution. The solvent was removed in vacuo, yielding 1.56 grams (51.9%) of the title product as a white solid. MS 265(M$^+$), mp 202°–205° C.

Analysis for $C_{18}H_{20}N_2 \cdot 2$ HCl: Theory: C, 71.87; H, 7.04; N, 9.31. Found: C, 72.02; H, 7.23; N, 9.05.

EXAMPLE 36

Synthesis of 1-phenyl-2-(2-trifluoromethylphenyl)benzimidazole

A solution of N-phenyl-o-phenylenediamine (1.84 g, 10 mmol) in diethyl ether (90 ml) was stirred at room temperature as an equimolar amount of 2-trifluoromethylbenzoyl chloride in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo to yield a red/brown oil.

The reaction product was further purified by trituration in diethyl ether to yield a white solid which was homogeneous on thin layer chromatography. mp 161°–162° C.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo to yield a red/brown mixture of oil and solid.

The reaction product was further purified by chromatography using a hexanes/ethyl acetate (3:1) solution as eluent followed by trituration in diethyl ether to yield 1.07 grams (37.2%). Recrystallization from hexanes yielded white crystals, homogeneous on thin layer chromatography. MS 338, mp 142°–144° C.

Analysis for $C_{20}H_{13}F_3N_2$: Theory: C, 71.00; H, 3.87; N, 8.28. Found: C, 70.70; H, 3.97; N, 8.12.

EXAMPLE 37

Synthesis of 1-benzyl-2-(3,4,5-trimethoxyphenyl)benzimidazole

A solution of o-phenylenediamine dihydrochloride (3.62 g, 20 mmol), 3,4,5-trimethoxybenzaldehyde (3.92 g, 20 mmol) and triethylamine (2.02 g, 20 moles) in nitrobenzene (100 mls) was heated at 150° C. for 32 hours. The majority of the nitrobenzene was distilled off by vacuum distillation (60° C. pot temperature, 0.1 mm Hg). The crude product was partitioned between 1N sodium hydroxide and ethyl acetate. The ethyl acetate fraction was removed and the aqueous phase was extracted with ethyl acetate (3×100 ml).

The organic fractions were combined, washed with brine, dried over sodium sulfate, filtered, and the solvents were removed in vacuo to yield a red brown oil which was purified by column chromatography using a hexanes/ethyl acetate (1:1) solution as the eluting solvent to yield the intermediate 2-(3,4,5-trimethoxyphenyl)benzimidazole. NMR The intermediate prepared above (0.91 g, 3.2 mmol) and sodium hydride (0.26 g, 6.4 mmol) in N,N-dimethylformamide (25 ml) were stirred at room temperature as benzyl bromide (0.60 g, 6.4 mmol) was added dropwise. The resulting mixture was stirred at room temperature for 30 minutes and then heated to 120° C. where it was maintained for seven days. Additional sodium hydride and benzymbromide were added as needed force the reaction forward.

The crude product was partitioned between water and ethyl acetate, followed by an acid/base workup in a separatory funnel. The organic layers were washed with brine, dried over potassium carbonate, filtered, and the solvents were removed in vacuo. MS 375(M$^+$)

Analysis for $C_{23}H_{22}N_2O_3$: Theory: C, 73.78; H, 5.92; N, 7.48. Found: C, 73.99; H, 5.95; N, 7.19.

EXAMPLES 38 AND 39

Synthesis of 1-phenylmethyl-2-(3,4,5-trimethoxyphenyl)-5-methoxybenzimidazole (Example 38) and 1-phenylmethyl-2-(3,4,5-trimethoxyphenyl)-6-methoxybenzimidazole (Example 39)

This synthesis was performed essentially as described in Example 37 except for the substitution of 4-methoxy-o-phenylenediamine in place of the o-phenylenediamine employed there. This resulted in a mixture of the regioisomers of the title products which could be separated using common techniques.

Example 38: MS 404, Analysis for $C_{24}H_{24}N_2O_4$: Theory: C, 71.27; H, 5.98; N, 6.92. Found: C, 71.07; H, 6.16; N, 6.89.

Example 39: MS 404, Analysis for $C_{24}H_{24}N_2O_4$: Theory: C, 71.27; H, 5.98; N, 6.93. Found: C, 71.24; H, 6.11; N, 6.97.

EXAMPLE 40

Synthesis of 1-(3-chlorobenzyl)-2-(3,4,5-trimethoxyphenyl) benzimidazole

An amount of 2-(3,4,5-trimethoxyphenyl)benzimidazole (1.05 g, 3.69 mmol), prepared as described in Example 37, supra, was added to a three-neck flask with a stir bar. The contents of the flask were placed under nitrogen atmosphere and 50 ml of N,N-dimethylformamide was added by syringe. This mixture was then allowed to stir. Sodium hydride (60%, 0.41 g, 4.10 mmol) was then added to the reaction mixture and the resulting mixture was stirred for about 30 minutes.

The resulting grayish mixture was then placed into an oil bath and 3-chlorobenzyl bromide (0.60 ml, 4.10 mmol) was added. The temperature of the solution was then raised to 60° C. and the solution was allowed to stir overnight.

The solution was then removed from the oil bath and allowed to cool to room temperature. Ethyl acetate (150 ml) was then added to the reaction mixture. This organic solution was extracted with water (3×150 ml), followed by 25 ml of diethyl ether. The organic phase was then washed with a saturated sodium chloride solution.

The organic solution was reduced in vacuo to yield a yellow oil. To this oil ethanol (50 ml) and hexanes (20 ml) were added. The yellow solution was cooled and allowed to crystallize. The crystals were recovered by filtration and then washed with 20 ml of hexanes. The liquors were reduced in vacuo and allowed to crystallize to yield a total of 1.05 grams of the title product. MS 409, 411, mp 83° C.

Analysis for $C_{23}H_{21}ClN_2O_3$: Theory: C, 67.56; H, 5.18; N, 6.85. Found: C, 67.82; H, 5.21; N, 6.64.

EXAMPLE 41

Synthesis of 1-(2-chlorobenzyl)-2-(3,4,5-trimethoxyphenyl) benzimidazole

The title product was prepared essentially as described in Example 40, supra, except that 2-chlorobenzyl bromide (0.50 ml, 4.19 mmol) was employed instead of the chlorobenzyl bromide, to yield 1.13 g (80%). MS 409, 411, mp 173.5° C.

Analysis for $C_{23}H_{21}ClN_2O_3$: Theory: C, 67.56; H, 5.18; N, 6.85. Found: C, 67.33; H, 5.21; N, 6.60.

EXAMPLE 42

Synthesis of 1-(4-chlorobenzyl)-2-(3,4,5-trimethoxyphenyl) benzimidazole

The title compound was prepared essentially as described in Example 40, supra, except that 4-chlorobenzyl bromide (0.75 g, 4.03 mmol) was employed instead of the 3-chlorobenzyl bromide. MS 409, 411, mp 169° C.

Analysis for $C_{23}H_{21}ClN_2O_3$: Theory: C, 67.56; H, 5.18; N, 6.85. Found: C, 68.07; H, 5.34; N, 6.46.

EXAMPLE 43

Synthesis of 1-(2-methylbenzyl)-2-(3,4,5-trimethoxyphenyl)benzimidazole

The title compound was prepared essentially as described in Example 40, supra, except that α-bromo-oxylene (0.55 g, 4.10 mmol) was employed instead of the 3-chlorobenzyl bromide. MS 389, mp 140.5° C.

Analysis for $C_{24}H_{24}N_2O_3$: Theory: C, 74.21; H, 6.23; N, 7.21. Found: C, 73.92; H, 6.25; N, 7.05.

EXAMPLE 44

Synthesis of 1-(3-methylbenzyl)-2-(3,4,5-trimethoxyphenyl)benzimidazole

The title compound was prepared essentially as described in Example 40, supra, except that α-bromo-m-xylene (0.55 g, 4.10 mmol) was employed instead of the 3-chlorobenzyl bromide. MS 389, mp 78° C.

Analysis for $C_{24}H_{24}N_2O_3$: Theory: C, 74.21; H, 6.23; N, 7.21. Found: C, 73.96; H, 6.34; N, 7.01.

EXAMPLE 45

Synthesis of 1-(3-methoxybenzyl)-2-(3,4,5-trimethoxyphenyl)-benzimidazole

The title compound was prepared essentially as described in Example 40, supra, except that 3-methoxybenzyl chloride (0.60 ml, 4.13 mmol) was employed instead of the 3-chlorobenzyl bromide. MS 405, mp 127° C.

Analysis for $C_{24}H_{24}N_2O_4$: Theory: C, 71.27; H, 5.98; N, 6.93. Found: C, 71.21; H, 6.04; N, 6.98.

EXAMPLE 46

Synthesis of 1-(4-methoxybenzyl)-2-(3,4,5-trimethoxyphenyl)-benzimidazole

The title compound was prepared essentially as described in Example 40, supra, except that 4-methoxybenzyl chloride (0.60 ml, 4.13 mmol) was employed instead of the 3-chlorobenzyl bromide. MS 405, mp 110.5° C.

Analysis for $C_{24}H_{24}N_2O_4$: Theory: C, 71.27; H, 5.98; N, 6.93. Found: C, 71.01; H, 6.01; N, 7.08.

EXAMPLE 47

Synthesis of 1-(2-methoxybenzyl)-2-(3,4,5-trimethoxyphenyl)-benzimidazole

The title compound was prepared essentially as described in Example 40, supra, except that 2-methoxybenzyl chloride (50% 1.26 ml, 4.13 mmol) was employed instead of the 3-chlorobenzyl bromide. This reaction was performed at room temperature and allowed to stir for about six hours. MS 405, mp 136° C.

Analysis for $C_{24}H_{24}N_2O_4$: Theory: C, 71.27; H, 5.98; N, 6.93. Found: C, 71.47; H, 6.13; N, 6.92.

EXAMPLE 48

Synthesis of 1-(2-fluorobenzyl)-2-(3,4,5-trimethoxyphenyl) benzimidazole

The title compound was prepared essentially as described in Example 40, supra, except that 2-fluorobenzyl bromide (0.48 ml, 4.33 mmol) was employed instead of the 3-chlorobenzyl bromide. MS 392, mp 153.5° C.

Analysis for $C_{23}H_{21}FN_2O_3$: Theory: C, 70.40; H, 5.39; N, 7.14. Found: C, 70.15; H, 5.37; N, 7.14.

EXAMPLE 49

Synthesis of 1-(2-trifluoromethylbenzyl)-2-(3,4,5-trimethoxyphenyl)-benzimidazole The title compound was prepared essentially as described in Example 40, supra, except that 2-trifluoromethylbenzyl bromide (0.48 ml, 4.33 mmol) was employed instead of the 3-chlorobenzyl bromide. MS 442, mp 144° C.

Analysis for $C_{24}H_{21}F_3N_2O_3$: Theory: C, 65.15; H, 4.78; N, 6.33. Found: C, 65.18; H, 4.75; N, 6.28.

EXAMPLE 50

Synthesis of 1-(2-iodobenzyl)-2-(3,4,5-trimethoxyphenyl) benzimidazole

The title compound was prepared essentially as described in Example 40, supra, except that 2-iodobenzyl bromide (1.0 ml, 4.33 mmol) was employed instead of the 3-chlorobenzyl bromide. MS 500, mp 179° C.

Analysis for $C_{23}H_{21}IN_2O_3$: Theory: C, 55.21; H, 4.23; N, 5.60. Found: C, 55.26; H, 4.27; N, 5.71.

EXAMPLE 51

Synthesis of 1-(2-bromobenzyl)-2-(3,4,5-trimethoxyphenyl) benzimidazole

The title compound was prepared essentially as described in Example 40, supra, except that 2-bromobenzyl bromide (1.0 ml, 4.33 mmol) was employed instead of the 3-chlorobenzyl bromide. MS 452, 454, mp 152° C.

Analysis for $C_{23}H_{21}BrN_2O_3$: Theory: C, 60.94; H, 4.67; N, 6.18. Found: C, 61.18; H, 4.62; N, 6.09.

EXAMPLE 52

Synthesis of 1-(2,6-dichlorobenzyl)-2-(3,4,5-trimethoxyphenyl)-benzimidazole

The title compound was prepared essentially as described in Example 40, supra, except that 2,6-dichlorobenzyl bromide (0.81 g, 4.10 mmol) was employed instead of the 3-chlorobenzyl bromide. mp 157° C. MS 443, 445, NMR, IR.

Analysis for $C_{23}H_{20}Cl_2N_2O_3$: Theory: C, 62.31; H, 4.55; N, 6.32. Found: C, 62.84; H, 4.57; N, 6.31.

EXAMPLE 53

Synthesis of 1-(3,4-dichlorobenzyl)-2-(3,4,5-trimethoxyphenyl)-benzimidazole

The title compound was prepared essentially as described in Example 40, supra, except that 3,4-dichlorobenzyl bromide (0.90 g, 4.45 mmol) was employed instead of the 3-chlorobenzyl bromide. mp 145° C., MS 443, 445, NMR, IR.

Analysis for $C_{23}H_{20}Cl_2N_2O_3$: Theory: C, 62.31; H, 4.55; N, 6.32. Found: C, 62.35; H, 4.65; N, 6.17.

EXAMPLE 54

Synthesis of 1-(2,4-dichlorobenzyl)-2-(3,4,5-trimethoxyphenyl)-benzimidazole

The title compound was prepared essentially as described in Example 40, supra, except that 2,4-dichlorobenzyl bromide (0.45 g, 2.23 mmol) was employed instead of the 3-chlorobenzyl bromide. mp 186° C. MS 443, 445, NMR, IR.

Analysis for $C_{23}H_{20}Cl_2N_2O_3$: Theory: C, 62.31; H, 4.55; N, 6.32. Found: C, 62.22; H, 4.65; N, 6.34.

EXAMPLE 55

Synthesis of 1-(4-methylbenzyl)-2-(3,4,5-trimethoxyphenyl)benzimidazole

The title compound was prepared essentially as described in Example 40, supra, except that 4-methylbenzyl bromide (0.45 g, 2.23 mmol) was employed instead of the 3-chlorobenzyl bromide. MS 389, mp 84.5° C.

Analysis for $C_{24}H_{24}N_2O_3$: Theory: C, 74.21; H, 6.23; N, 7.21. Found: C, 73.91; H, 6.23; N, 6.98.

EXAMPLE 56

Synthesis of 1-(2-chlorobenzyl)-2-(3-methylphenyl)benzimidazole

The intermediate 2-(3-methylphenyl)benzimidazole was prepared by first mixing reacting 1-amino-2-nitrobenzene (8.50 g, 61.54 mmol) with toluene (180 ml) and heating to 100° C. To this mixture was then added 20 ml of N,N-diethylaniline and the reaction vessel was placed under a nitrogen atmosphere. To this solution was then added 3-methylbenzoyl chloride (24 ml, 132 mmol) and this mixture was then stirred overnight.

After stirring, the reaction mixture was neutralized by the addition of 300 ml of 1N hydrochloric acid and 300 ml of ethyl acetate. This was then stirred for about 30 minutes. The organic phase was then removed and washed with water, followed by drying over magnesium sulfate and reduction in vacuo, yielding yellow crystals of the intermediate 1-[(3-methylphenyl)carbonylamino]-2-nitrobenzene. The nitro group of the above intermediate was then reduced by catalytic hydrogenation employing a palladium on activated carbon catalyst resulting in the substituted 1,2-phenylenediamine.

The substituted 1,2-phenylenediamine (1.01 g, 4.46 mmol) was then cyclized using phosphorous oxychloride (1.01 g, 6.6 mmol) as described supra to produce 2-(3-methylphenyl)benzimidazole.

The title compound was then produced by reacting the 2-(3-methylphenyl)benzimidazole (0.75 g, 3.60 mmol) with 2-chlorobenzyl chloride (0.50 ml, 4.19 mmol) essentially as described in Example 40, supra. MS 332, 334, mp 117° C.

Analysis for $C_{21}H_{17}ClN_2$: Theory: C, 75.78; H, 5.15; N, 8.42. Found: C, 75.99; H, 5.24; N, 8.43.

The following compounds were synthesized essentially as described in Example 56 by reacting 2-(3-methylphenyl)benzimidazole with the appropriately substituted benzyl halide.

EXAMPLE 57

1-(3-Chlorobenzyl)-2-(3-methylphenyl)benzimidazole. MS 332, 334, mp 90° C.

Analysis for $C_{21}H_{17}ClN_2$: Theory: C, 75.78; H, 5.15; N, 8.42. Found: C, 75.51; H, 5.20; N, 8.56.

EXAMPLE 58

1-(4-Chlorobenzyl)-2-(3-methylphenyl)benzimidazole. MS 332, 334, mp 108.5° C.

Analysis for $C_{21}H_{17}ClN_2$: Theory: C, 75.78; H, 5.15; N, 8.42. Found: C, 75.55; H, 5.29; N, 8.37.

EXAMPLE 60

1-(2-Bromobenzyl)-2-(3-methylphenyl)benzimidazole. MS 376, 378, mp 134° C.

Analysis for $C_{21}H_{17}BrN_2$: Theory: C, 66.85; H, 4.54; N, 7.42. Found: C, 67.13; H, 4.60; N, 7.34.

EXAMPLE 61

1-(2-Iodobenzyl)-2-(3-methylphenyl)benzimidazole. MS 424, 425, mp 129° C.

Analysis for $C_{21}H_{17}IN_2 \cdot 0.1$ hexanes: Theory: C, 59.93; H, 4.28; N, 6.47. Found: C, 60.20; H, 4.12; N, 6.87.

EXAMPLE 62

1-(2,6-Dichlorobenzyl)-2-(3-methylphenyl)benzimidazole.

mp 148° C., NMR, IR, MS 366, 368.

Analysis for $C_{21}H_{16}Cl_2N_2 \cdot 0.1$ hexanes: Theory: C, 69.02; H, 4.67; N, 7.45. Found: C, 69.25; H, 4.42; N, 7.21.

EXAMPLE 63

1-(2,4-Dichlorobenzyl)-2-(3-methylphenyl)benzimidazole.

mp 161° C., MS 366, 368, IR, NMR.

Analysis for $C_{21}H_{16}Cl_2N_2$: Theory: C, 68.68; H, 4.39; N, 7.63. Found: C, 68.48; H, 4.61; N, 7.70.

EXAMPLE 64

1-(3,4-Dichlorobenzyl)-2-(3-methylphenyl)benzimidazole.

mp 85.5° C., MS 366, 368, IR, NMR.

Analysis for $C_{21}H_{16}Cl_2N_2$: Theory: C, 68.68; H, 4.39; N, 7.63. Found: C, 68.88; H, 4.41; N, 7.50.

EXAMPLE 65

1-(3-Methoxybenzyl)-2-(3-methylphenyl)benzimidazole.

Oil at room temperature. NMR, IR, MS 328.

Analysis for $C_{22}H_{20}N_2O$: Theory: C, 80.46; H, 6.14; N, 8.53. Found: C, 81.39; H, 6.70; N, 8.23.

EXAMPLE 66

1-(4-Methoxybenzyl)-2-(3-methylphenyl)benzimidazole.

mp 91° C., NMR, IR, MS 328.

Analysis for $C_{22}H_{20}N_2O$: Theory: C, 80.46; H, 6.14; N, 8.53. Found: C, 80.68; H, 6.31; N, 8.63.

EXAMPLE 67

Synthesis of 1-(3-hydroxybenzyl)-2-(3-methylphenyl)benzimidazole hydrobromide.

This compound was prepared by first synthesizing 1-(3-methoxybenzyl)-2-(3-methylphenyl)benzimidazole as described in Example 65, supra. With an amount of the compound of Example 65 (4.31 g, 13.12 mmol) in glacial acetic acid (50 ml) and hydrobromic acid (300 ml of a 48% w/v in acetic acid solution). This mixture was stirred for 2 hours while warming to reflux. The mixture was then stirred at reflux for about three hours.

The reaction mixture was then allowed to cool to room temperature after which time the reaction mixture was partitioned between water (1 liter) and methylene chloride, followed by extraction with methylene chloride (3×500 ml). The organic fractions were combined and dried over magnesium sulfate. After reducing the volume of the organic solvents in vacuo, the organic fraction was washed with water (3×250 ml) to remove residual hydrobromic acid. The orgnaic phases were combined and dried in vacuo to yield a gray solid which was washed with diethyl ether (2×250 ml) and dried in a vacuum oven. NMR, IR, MS 314, mp 235° C.

Analysis for $C_{21}H_{18}N_2O \cdot HBr$: Theory: C, 63.81; H, 4.84; N, 7.09. Found: C, 64.45; H, 5.02; N, 7.23.

EXAMPLE 69

Synthesis of 1-benzyl-2-(3,4,5-trimethoxyphenyl)-6-(hydroxy)-benzimidazole hydrochloride.

The title compound was prepared by first reacting 4-amino-3-nitrophenol (25.0 g, 162.2 mmol) with 3,4,5-trimethoxybenzoyl chloride (112 g, 485.6 mmol) in N,N-diethylaniline (69 ml) and toluene (500 ml). The reaction mixture was stirred and the temperature was raised to 100° C. The solution was maintained at this temperature for about 6 hours as a yellow precipitate formed. The reaction mixture was then partitioned between 1N hydrochloric acid (250 ml) and ethyl acetate (250 ml). The crystals were then removed by filtration and washed with ethyl acetate (300 ml) and water (300 ml) to yield the intermediate 1-(3,4,5-trimethoxy)benzyl ester of 4-(3,4,5-trimethoxyphenylcarbonylamino)-2-nitrophenol.

A benzyl group was then substituted on the nitro group by reacting the above intermediate (10 g, 18.4 mmol) with benzaldehyde (6 ml) in N,N-dimethylformamide (100 ml) under a hydrogen atmosphere (60° C. at 60 p.s.i.) with 6.0 g of a palladium on activated carbon catalyst.

The benzimidazole ring was closed using phosphorous oxychloride in chloroform as described supra. The ester on the 6-hydroxy group of the benzimidazole was removed by incubating the intermediate in 1N sodium hydroxide (500 ml) and tetrahydrofuran (500 ml). This solution was stirred overnight, followed by acidification with a sufficient amount of 1N hydrochloric acid to reduce the pH to 1.0. This solution was then washed with ethyl acetate (2×500 ml). The organic fractions were combined, dried over magnesium sulfate, and the solvents removed in vacuo to yield a brownish/red solid. The title compound was further purified by flash chromatography to yield a grayish solid. MS 390.

Analysis for $C_{23}H_{22}N_2O_4 \cdot HCl$: Theory: C, 64.71; H, 5.43; N, 6.56. Found: C, 65.12; H, 5.40; N, 6.63.

EXAMPLE 70

Synthesis of 1-benzyl-2-(3,4,5-trimethoxyphenyl)-6-[2-(4-morpholinyl)ethoxy]benzimidazole.

The title compound was prepared by reacting the compound of Example 69, supra, (0.23 g, 0.59 mmol) with 4-(2-chloroethyl)morpholine hydrochloride (1.10 g, 5.91 mmol) and potassium carbonate (1.63 g, 11.80 mmol) in acetone. The reaction conditions employed were essentially as described for previous alkylations. MS 503.

Analysis for $C_{29}H_{33}N_3O_5$: Theory: C, 69.17; H, 6.60; N, 8.34. Found: C, 69.10; H, 6.70; N, 8.42.

EXAMPLE 71

Synthesis of 1-benzyl-2-(3,4,5-trimethoxyphenyl)-6-[2-(1-piperidinyl)ethoxy]benzimidazole.

The title compound was prepared essentially as described in Example 70 except that 1-(2-chloroethyl)piperidine hydrochloride was employed in place of 4-(2-chloroethyl)morpholine hydrochloride. MS 501.

Analysis for $C_{30}H_{35}N_3O_4$: Theory: C, 71.83; H, 7.03; N, 8.38. Found: C, 71.95; H, 7.27; N, 8.17.

EXAMPLE 72

Synthesis of 1-benzyl-2-(3,4,5-trimethoxyphenyl)-6-[2-(1-pyrroldinyl)ethoxy]benzimidazole.

The title compound was prepared essentially as described in Example 70 except that 1-(2-chloroethyl)pyrrolidine hydrochloride was employed in place of 4-(2-chloroethyl)morpholine hydrochloride. MS 488.

Analysis for $C_{29}H_{33}N_3O_4$: Theory: C, 71.44; H, 6.82; N, 8.62. Found: C, 71.61; H, 7.05; N, 8.87.

EXAMPLE 73

Synthesis of 1-benzyl-2-(3,4,5-trimethoxyphenyl)-6-[2-(1-hexamethyleneiminyl)ethoxy]benzimidazole.

The title compound was prepared essentially as described in Example 70 except that 1-(2-chloroethyl)hexamethyleneimine hydrochloride was employed in place of 4-(2-chloroethyl)morpholine hydrochloride. NMR, IR, MS 515, mp 122.5° C.

Analysis for $C_{31}H_{37}N_3O_4$: Theory: C, 72.21; H, 7.23; N, 8.15. Found: C, 72.18; H, 7.19; N, 8.42.

EXAMPLE 74

Synthesis of 1-benzyl-2-(3,4,5-trimethoxyphenyl)-6-[3-(1-piperidinyl)propoxy]benzimidazole.

The title compound was prepared essentially as described in Example 70 except that 1-(3-chloropropyl)piperidine hydrochloride was employed in place of 4-(2-chloroethyl)morpholine hydrochloride. mp 92° C., NMR, IR, MS 515.

Analysis for $C_{31}H_{37}N_3O_4$: Theory: C, 72.21; H, 7.23; N, 8.15. Found: C, 72.50; H, 7.26; N, 7.90.

EXAMPLE 75

Synthesis of 1-benzyl-2-(3,4,5-trimethoxyphenyl)-6-(3-chloropropoxy)benzimidazole.

The title compound was prepared essentially as described in Example 70 except that 1-chloro-3-iodopropane was employed in place of 4-(2-chloroethyl)morpholine hydrochloride. mp 118.5° C., MS 466, 468, NMR, IR.

Analysis for $C_{26}H_{27}ClN_2O_4 \cdot 0.5\ H_2O$: Theory: C, 65.61; H, 5.93; N, 5.89. Found: C, 65.92; H, 5.74; N, 5.91.

EXAMPLE 76

Synthesis of 1-benzyl-2-(3,4,5-trimethoxyphenyl)-6-(2-chloroethoxy)benzimidazole.

The title compound was prepared essentially as described in Example 70 except that 1-bromo-2-chloroethane was employed in place of 4-(2-chloroethyl)morpholine hydrochloride. IR, NMR, MS 452, 454, mp 129° C.

Analysis for $C_{25}H_{25}ClN_2O_4$: Theory: C, 66.30; H, 5.56; N, 6.19. Found: C, 67.33; H, 5.41; N, 6.61.

EXAMPLE 77

Synthesis of 1-benzyl-2-(3,4,5-trimethoxyphenyl)-6-[2-[4-(piperidin-1-yl) piperdin-1-yl]ethoxy]benzimidazole.

The title compound was prepared by reacting the compound of Example 76, supra, (0.45 g, 1.0 mmol) with 4-(piperdin-1-yl)piperidine (2.0 g, 11.9 mmol) in the presence of the base N,N-diisopropylethylamine, tetra-n-butylammonium iodide and acetonitrile at 80° C. After incubating overnight at 80° C. the reaction was washed with water (2×500 ml), followed by a wash with a saturated sodium chloride solution (1×500 ml). The organic phase was then dried over potassium carbonate and the solvents were removed in vacuo to yield a light brown oil. The desired product was purified by chromatography and triturated with diethyl ether to yield a light brown powder, which was removed by filtration and washed with diethyl ether to yield the purified title compound. MS 584, 585, NMR, IR, mp 143° C.

Analysis for $C_{35}H_{44}N_4O_4$: Theory: C, 71.89; H, 7.58; N, 9.58. Found: C, 72.11; H, 7.62; N, 9.67.

EXAMPLE 78

Synthesis of 1-benzyl-2-(3,4,5-trimethoxyphenyl)-6-[1-methyl-2-(N,N-dimethylamino)]ethoxy]benzimidazole.

The title compound was prepared by reacting the compound of Example 70, supra, 0.45 g, 1.15 mmol) with 1-methyl-2-dimethylaminoethyl chloride (1.82 g, 11.51 mmol) and potassium chloride (3.18 g, 23.01 mmol) in 100 ml of acetone. The reactants were admixed and then heated to reflux overnight.

After the overnight incubation the reaction mixure was acidified by adding 500 ml of 1N hydrochloric acid and then washed with ethyl acetate (2×250 ml). The aqueous layer was then basified and extracted with ethyl acetate (500 ml). The organic fractions were combined and washed with a saturated sodium chloride solution and dried over potassium carbonate. The solvents were removed in vacuo to yield a yellow oil which was triturated with hexanes, forming a white solid. This was further purified by crystallizing from 10:1 hexanes:ethanol to yield the desired title product. IR, NMR, MS 475, 476, mp 93° C.

Analysis for $C_{28}H_{33}N_3O_4$: Theory: C, 70.71; H, 6.99; N, 8.84. Found: C, 70.93; H, 7.01; N, 8.92.

EXAMPLE 79

Synthesis of 1-benzyl-2-(3,4,5-trimethoxyphenyl)-6-[2-(N,N-dimethylamino)ethoxy]benzimidazole.

The title compound was prepared essentially as described in Example 78, supra, except that 2-dimethylaminoethyl chloride was employed in place of the 1-methyl-2-dimethylaminoethyl chloride. IR, NMR, MS 461, mp 108° C.

Analysis for $C_{27}H_{31}N_3O_4 \cdot 0.1$ hexanes: Theory: C, 70.51; H, 6.95; N, 8.94. Found: C, 70.98; H, 6.60; N, 8.62.

EXAMPLE 80

Synthesis of 1-benzyl-2-(3,4,5-trimethoxyphenyl)-6-[3-(N,N-dimethylamino)propoxy]benzimidazole.

The title compound was prepared essentially as described in Example 78, supra, except that 3-dimethylaminopropyl chloride was employed in place of the 1-methyl-2-dimethylaminoethyl chloride. IR, NMR, MS 475, mp 112° C.

Analysis for $C_{28}H_{33}N_3O_4$: Theory: C, 70.71; H, 6.99; N, 8.83. Found: C, 70.42; H, 6.97; N, 8.68.

EXAMPLE 81

Synthesis of 1-benzyl-2-(3,4,5-trimethoxyphenyl)-6-[2-(N,N-diisopropylamino)ethoxy]benzimidazole.

The title compound was prepared essentially as described in Example 78, supra, except that 2-diisopropylaminoethyl chloride was employed in place of the 1-methyl-2-dimethylaminoethyl chloride. IR, NMR, MS 517, 518, mp 101° C.

Analysis for $C_{31}H_{39}N_3O_4$: Theory: C, 71.93; H, 7.59; N, 8.12. Found: C, 71.91; H, 7.76; N, 7.98.

EXAMPLE 83

Synthesis of 1-benzyl-2-(3,4,5-trimethoxyphenyl)-6-[2-(4-methyl-1-piperazinyl)ethoxy]benzimidazole.

The title compound was prepared essentially as described in Example 77, supra, employing the compound of Example 76, except that 1-methylpiperazine was employed in place of the 4-(piperdin-1-yl)piperidine. IR, NMR, MS 517, mp 113° C.

Analysis for $C_{30}H_{36}N_4O_4 \cdot 0.5\ H_2O$: Theory: C, 68.55; H, 7.09; N, 10.66. Found: C, 68.83; H, 7.19; N, 10.98.

EXAMPLE 84

Synthesis of 1-benzyl-2-(3-methylphenyl)-6-hydroxybenzimidazole

The title compound was prepared essentially as described in Example 69, supra, except that 3-methylbenzoyl chloride (18.8 g, 121.6 mmol) was employed instead of the 3,4,5-trimethoxybenzoyl chloride. MS 314

Analysis for $C_{21}H_{18}N_2O$: Theory: C, 80.23; H, 5.77; N, 8.91. Found: C, 80.10; H, 5.85; N, 8.81.

EXAMPLE 85

Synthesis of 1-benzyl-2-(3-methylphenyl)-6-[2-(1-piperidinyl)ethoxy]benzimidazole The title compound was synthesized by reacting the compound of Example 84, supra, (0.25 g, 0.79 mmol) with 2-(piperdinyl-1-yl)ethyl chloride (17.46 g, 7.9 mmol) in the presence of potassium carbonate (2.20 g, 15.9 mmol) and acetone (150 ml). These contents were added to a flask and refluxed overnight.

After the overnight incubation, the reaction mixture was quenched by adding 0.5N hydrochloric acid (300 ml) and was washed with ethyl acetate (300 ml). The aqueous layer was basified with 1N sodium hydroxide until the pH=10. This aqueous layer was extracted with ethyl acetate (300 ml). The organic fractions were combined and the solvent volume was reduced in vacuo, leaving a yellow oil. Diethyl ether and hexanes were added to this oil and it was then placed at −20° C. until crystals of the title product formed, which were then harvested by filtration. MS 425, 426.

Analysis for $C_{28}H_{31}N_3O$: Theory: C, 79.03; H, 7.34; N, 9.87. Found: C, 78.75; H, 7.47; N, 10.09.

EXAMPLE 86

Synthesis of 1-benzyl-2-(3-methylphenyl)-6-[2-(1-pyrrolidinyl)ethoxy]benzimidazole The title product was prepared essentially as described in Example 85, supra, except that 1-(2-chloroethyl)pyrrolidine hydrochloride was employed instead of the 2-(piperdinyl-1-yl)ethyl chloride. MS 411.

Analysis for $C_{27}H_{29}N_3O$: Theory: C, 78.80; H, 7.10; N, 10.21. Found: C, 78.85; H, 7.14; N, 10.08.

EXAMPLE 87

Synthesis of 1-benzyl-2-(3-methylphenyl)-6-[2-(4-morpholinyl)ethoxy]benzimidazole The title product was prepared essentially as described in Example 85, supra, except that 4-(2-chloroethyl)morpholine hydrochloride was employed instead of the 2-(piperdinyl-1-yl)ethyl chloride. MS 427.

Analysis for $C_{27}H_{29}N_3O_2$: Theory: C, 75.85; H, 6.84; N, 9.83. Found: C, 75.75; H, 6.89; N, 9.88.

EXAMPLE 88

Synthesis of 1-benzyl-2-(3-methylphenyl)-6-[2-(N,N-dimethylamino)ethoxy]benzimidazole The title product was prepared essentially as described in Example 85, supra, except that 2-(N,N-dimethylamino)ethyl chloride was employed instead of the 2-(piperdinyl-1-yl) ethyl chloride. MS 385.

Analysis for $C_{25}H_{27}N_3O$: Theory: C, 77.89; H, 7.06; N, 10.90. Found: C, 77.88; H, 7.14; N, 10.74.

EXAMPLE 89

Synthesis of 1-benzyl-2-(3-methylphenyl)-6-[2-(N,N-dibenzylamino)ethoxy]benzimidazole The title product was prepared essentially as described in Example 85, supra, except that 2-(N,N-dibenzylamino)ethyl chloride was employed instead of the 2-(piperdinyl-1-yl) ethyl chloride. MS 537.

Analysis for $C_{37}H_{35}N_3O$: Theory: C, 82.65; H, 6.56; N, 7.82. Found: C, 82.47; H, 6.73; N, 7.81.

EXAMPLE 90

Synthesis of 1-benzyl-2-(3-methylphenyl)-6-[2-(N-phenyl-N-ethylamino)ethoxy]benzimidazole The title product was prepared essentially as described in Example 85, supra, except that 2-(N-benzyl-N-ethylamino) ethyl chloride was employed instead of the 2-(piperdinyl-1-yl)ethyl chloride. MS 461, 462.

Analysis for $C_{31}H_{31}N_3O$: Theory: C, 80.66; H, 6.77; N, 9.10. Found: C, 80.37; H, 6.81; N, 8.98.

EXAMPLE 91

Synthesis of 1-benzyl-2-(3-methylphenyl)-6-[2-(N,N-isopropylamino)ethoxy]benzimidazole The title product was prepared essentially as described in Example 85, supra, except that 2-(N,N-diisopropylamino) ethyl chloride was employed instead of the 2-(piperdinyl-1-yl)ethyl chloride. MS 441.

Analysis for $C_{29}H_{35}N_3O$: Theory: C, 78.87; H, 7.99; N, 5.51. Found: C, 79.07; H, 8.12; N, 5.60.

EXAMPLE 92

Synthesis of 1-benzyl-2-(3-methylphenyl)-6-[2-(hexamethyleneimin-1-yl)ethoxy]benzimidazole The title product was prepared essentially as described in Example 85, supra, except that 2-(hexamethyleneimin-1-yl)ethyl chloride was employed instead of the 2-(piperdinyl-1-yl)ethyl chloride. MS 439.

Analysis for $C_{29}H_{33}N_3O$: Theory: C, 79.23; H, 7.57; N, 9.56. Found: C, 79.45; H, 7.72; N, 9.66.

EXAMPLE 93

Synthesis of 1-benzyl-2-(3-methylphenyl)-6-[2-(N,N-diethylamino)ethoxy]-benzimidazole The title product was prepared essentially as described in Example 85, supra, except that 2-(N,N-diethylamino)ethyl chloride was employed instead of the 2-(piperdinyl-1-yl) ethyl chloride. MS 413, 414.

Analysis for $C_{27}H_{31}N_3O \cdot 0.25\ H_2O$: Theory: C, 77.57; H, 7.59; N, 10.05. Found: C, 77.60; H, 7.42; N, 9.74.

EXAMPLE 94

Synthesis of 1-benzyl-2-{3-methylphenyl)-6-[3-(N,N-dimethylamino)propoxy]benzimidazole The title product was prepared essentially as described in Example 85, supra, except that 3-{N,N-dimethylamino)propyl chloride was employed instead of the 2-(piperdinyl-1-yl)ethyl chloride. MS 399.

Analysis for $C_{26}H_{29}N_3O$: Theory: C, 78.16; H, 7.32; N, 10.52. Found: C, 77.93; H, 7.32; N, 10.25.

EXAMPLE 95

Synthesis of 1-benzyl-2-(3-methylphenyl)-6-[3-(piperdin-1-yl)propoxy]-benzimidazole The title product was prepared essentially as described in Example 85, supra, except that 3-(piperidin-1-yl)propyl chloride was employed instead of the 2-(piperdinyl- 1-yl) ethyl chloride. mp 84° C., MS 439, NMR, IR.

Analysis for $C_{29}H_{33}N_3O$: Theory: C, 79.23; H, 7.57; N, 9.55. Found: C, 79.39; H, 7.59; N, 9.59.

EXAMPLE 96

Synthesis of 1-benzyl-2-(3-methylphenyl)-6-[2- N,N-dimethylamino)propoxy]-benzimidazole The title product was prepared essentially as described in Example 85, supra, except that 2-(N,N-dimethylamino)propyl chloride was employed instead of the 2-(piperdinyl-1-yl) ethyl chloride. mp 74° C., NMR, IR, MS 399,400.

Analysis for $C_{26}H_{29}N_3O$: Theory: C, 78.16; H, 7.32; N, 10.52. Found: C, 79.58; H, 7.44; N, 10.49.

EXAMPLE 97

Synthesis of 1-benzyl-2-(3-methylphenyl)-6-(3chloropropoxy)-benzimidazole

The title product was prepared essentially as described in Example 85, supra, except that 3-chloropropyl iodide was employed instead of the 2-(piperdinyl-1-yl)ethyl chloride. mp 97° C., NMR, IR, MS 390, 391.

Analysis for $C_{24}H_{23}ClN_2O$: Theory: C, 73.74; H, 5.93; N, 7.17. Found: C, 73.61; H, 5.94; N, 7.39.

EXAMPLE 98

Synthesis of 1-benzyl-2-(3-methylphenyl)-6-(2-chloroethoxy)-benzimidazole

The title product was prepared essentially as described in Example 85, supra, except that 2-chloroethyl bromide was employed instead of the 2-(piperdinyl-1-yl)ethyl chloride. mp 88° C., MS 376, 378, NMR, IR.

Analysis for $C_{23}H_{21}ClN_2O$: Theory: C, 73.30; H, 5.62; N, 7.43. Found: C, 73.04; H, 5.67; N, 7.65.

EXAMPLE 99

Synthesis of 1-benzyl-2-(3-methylphenyl)-6-[3-(morpholin-4-yl)propoxy)-benzimidazole The title compound was prepared by first adding morpholine (1.02 g, 11.77 mmol) and the compound of Example 97, supra, (0.39 g, 1.00 mmol) to 125 ml of acetonitrile while stirring under nitrogen purge. To this mixture is then added diisopropylethyl aniline (1.51 ml, 8.67 mmol) dropwise. This reaction mixture is then allowed to stir overnight.

After the overnight stirring, additional diisopropyl aniline (1.00 ml) is added and the mixture is then heated to 60° C. and maintained at this temperature for about 3 days. The reaction mixture was then washed with water (3×250 ml) and the solvents were removed in vacuo, resulting in a yellow oil.

The yellow oil was further purified by chromatography using ethyl acetate, followed by removal of the solvents in vacuo, and trituration with hexanes to afford yellow crystals. NMR, MS 441, IR, mp 120° C.

Analysis for $C_{28}H_{31}N_3O_2$: Theory: C, 76.16; H, 7.08; N, 9.52. Found: C, 76.39; H, 7.26; N, 9.54.

EXAMPLE 100

Synthesis of 1-benzyl-2-(3-methylphenyl)-6-[3-(pyrrolidin-1-yl)propoxy)-benzimidazole The title compound was prepared essentially as described in Example 99, supra, except that pyrrolidine was employed in place of morpholine. mp 120° C., NMR, IR, MS 425.

Analysis for $C_{28}H_{31}N_3O$: Theory: C, 79.03; H, 7.34; N, 9.87. Found: C, 79.22; H, 7.39; N, 9.83.

EXAMPLE 101

Synthesis of 1-benzyl-2-(3-methylphenyl)-6-[3-(hexamethyleneimin-1-yl)propoxy)-benzimidazole The title compound was prepared essentially as described in Example 99, supra, except that hexamethyleneimine was employed in place of morpholine. mp 69.5° C., NMR, IR, MS 453, 454.

Analysis for $C_{30}H_{35}N_3O$: Theory: C, 79.43; H, 7.78; N, 9.26. Found: C, 79.60; H, 7.88; N, 9.28.

EXAMPLE 102

Synthesis of 1-benzyl-2-(3-methylphenyl)-6-[3-(heptamethyleneimin-1-yl)propoxy)benzimidazole The title compound was by reacting the compound of Example 97, supra, (0.39 g, 1.00 mmol) with heptamethyleneimine (10 g, 88.3 mmol) in the presence of N,N-diisopropylethylamine (2 ml) and acetonitrile (5 ml). This reaction mixture was raised to 80° C. and allowed to stir at that temperature overnight. The compound was purified essentially as described in Example 99, supra. NMR, MS 467, mp 77° C.

Analysis for $C_{31}H_{37}N_3O$: Theory: C, 79.62; H, 7.97; N, 8.98. Found: C, 79.50; H, 7.99; N, 8.99.

EXAMPLE 103

Synthesis of 1-benzyl-2-(3-methylphenyl)-6-[2-(4-methylpiperazin-1-yl)ethoxy]benzimidazole The title compound was prepared by reacting the compound of Example 98, supra, (1.89 g, 5.01 mmol) with 1-methyl-piperazine (65 ml) in the presence of N,N-diisopropylethyl amine (4 ml) and N,N-dimethylformamide (100 ml) under nitrogen atmosphere. This reaction mixture was heated to 50° C. and stirred overnight at that temperature. The compound was purified essentially as described in Example 99, supra. NMR, IR, MS 440, 441, mp 91° C.

Analysis for $C_{28}H_{32}N_4O$: Theory: C, 76.33; H, 7.32; N, 12.72. Found: C, 76.19; H, 7.15; N, 12.96.

EXAMPLE 104

Synthesis of 1-(2-trifluoromethylbenzyl)-2-(3,4,5-trimethoxyphenyl)- 6-hydroxybenzimidazole The title compound was prepared by first reacting 3,4,5-trimethoxybenzoyl chloride (112.0 g, 485.6 mmol) with 4-amino-3-nitrophenol (25.0 g, 162.2 mmol) in N,N-diethylaniline (69 ml) and toluene (500 ml). This reaction mixture was heated to 100° C. and maintained at that temperature for about 6 hours. The intermediate ester of 4-(3,4,5-trimethoxyphenylcarbonylamino)-3-nitrophenol was purified essentially as described in Example 69, supra.

The nitro moiety of the above-described intermediate was reduced to an amino group by catalytic hydrogenation using a palladium on activated carbon catalyst as described previously. This primary amino group was then alkylated by reacting with 2-trifluoromethylbenzyl bromide in the presence of N,N-diisopropylethyl amine and tetrahydrofuran. This mixture was allowed to reflux overnight The reaction mixture was then washed with water (5×500 ml) followed by a wash with saturated sodium chloride (500 ml). The organic phase was dried over potassium carbonate, and the solvents were removed in vacuo, leaving a brown solid. Following trituration in diethyl ether a gray solid formed.

The benzimidazole ring was closed using phosphorous oxychloride in chloroform as previously described. The protecting ester on the 6-hydroxy of the benzimidazote ring was removed by incubating the protected compound in 1N sodium hydroxide in tetrahydrofuran to cleave this group, leaving the title compound. NMR, IR, MS 458, mp 191° C.

Analysis for $C_{24}H_{21}F_3N_2O_4$: Theory: C, 62.88; H, 4.62; N, 6.11. Found: C, 62.89; H, 4.88; N, 5.90.

EXAMPLE 105

Synthesis of 1-(2-trifluoromethylbenzyl)-2-(3,4,5-trimethoxyphenyl)- 6-[2-(piperidin-1-yl)ethoxy]benzimidazole The title compound was prepared by reacting the compound of Example 104 with 1-(2-chloroethyl)piperidine hydrochloride essentially as previously described. mp 167° C., NMR, IR, MS 570.

Analysis for $C_{31}H_{34}F_3N_3O_4$: Theory: C, 65.37; H, 6.02; N, 7.38. Found: C, 65.40; H, 6.02; N, 7.41.

EXAMPLE 106

Synthesis of 1-(2-trifluoromethylbenzyl)-2-(3,4,5-trimethoxyphenyl)- 6-[2-(N,N-dimethylamino)propoxy]benzimidazole The title compound was prepared by reacting the compound of Example 104 with 2-(N,N-dimethylamino)propyl chloride essentially as previously described. mp 163° C., NMR, IR, MS 543, 544.

Analysis for $C_{29}H_{32}F_3N_3O_4$: Theory: C, 64.08; H, 5.93; N, 7.73. Found: C, 64.00; H, 5.86; N, 7.68.

EXAMPLE 107

Synthesis of 1-{2-trifluoromethylbenzyl)-2-(3,4,5-trimethoxyphenyl)- 6-[2-(N,N-dimethylamino)ethoxy]benzimidazole The title compound was prepared by reacting the compound of Example 104 with 2-(N,N-dimethylamino)ethyl chloride essentially as previously described. mp 151° C., NMR, IR, MS 529.

Analysis for $C_{28}H_{30}F_3N_3O_4$: Theory: C, 63.51; H, 5.71; N, 7.94. Found: C, 63.79; H, 5.57; N, 8.02.

EXAMPLE 108

Synthesis of 1-(2-trifluoromethylbenzyl)-2-(3,4,5-trimethoxyphenyl)- 6-[3-(N,N-dimethylamino)propoxy]benzimidazole The title compound was prepared by reacting the compound of Example 104 with 3-(N,N-dimethylamino)propyl chloride essentially as previously described. mp 142° C., NMR, IR, MS 543.

Analysis for $C_{29}H_{32}F_3N_3O_4$: Theory: C, 64.08; H, 5.93; N, 7.73. Found: C, 64.33; H, 5.78; N, 7.47.

EXAMPLE 109

Synthesis of 1-(2-trifluoromethylbenzyl)-2-(3,4,5-trimethoxyphenyl)- 6-[3-(piperidin-1-yl)propoxy]benzimidazole The title compound was prepared by reacting the compound of Example 104 with 3-(piperidin-1-yl)propyl chloride essentially as previously described. mp 138° C., IR, NMR, MS. 584

Analysis for $C_{32}H_{36}F_3N_3O_4$: Theory: C, 65.85; H, 6.22; N, 7.20. Found: C, 65.74; H, 6.07; N, 7.35.

EXAMPLE 110

Synthesis of 1-(2-trifluoromethylbenzyl)-2-(3,4,5-trimethoxyphenyl)- 6-[2-(hexamethyleneimin-1-yl)ethoxy] benzimidazole The title compound was prepared by reacting the compound of Example 104 with 2-(hexamethyleneimin-1-yl) ethyl chloride essentially as previously described. mp 156° C., IR, NMR, MS 583,584.

Analysis for $C_{32}H_{36}F_3N_3O_4$: Theory: C, 65.85; H, 6.22; N, 7.20. Found: C, 65.59; H, 5.98; N, 7.33.

EXAMPLE 111

Synthesis of 1-(2-trifluoromethylbenzyl)-2-(3,4,5-trimethoxyphenyl)- 6-[2-(pyrrolidin-1-yl)ethoxy]benzimidazole The title compound was prepared by reacting the compound of Example 104 with 2-(pyrrolidin-1-yl)ethyl chloride essentially as previously described. mp 143° C., NMR, IR, MS 555.

Analysis for $C_{30}H_{32}F_3N_3O_4$: Theory: C, 64.85; H, 5.80; N, 7.56. Found: C, 64.93; H, 5.87; N, 7.54.

EXAMPLE 112

Synthesis of 1-(2-trifluoromethylbenzyl)-2-(3,4,5-trimethoxyphenyl)- 6-[2-(morpholin-4-yl)ethoxy]benzimidazole The title compound was prepared by reacting the compound of Example 104 with 2-(morpholin-4-yl)ethyl chloride essentially as previously described. mp 175° C., NMR, IR, MS 572.

Analysis for $C_{30}H_{32}F_3N_3O_5$: Theory: C, 63.04; H, 5.64; N, 7.35. Found: C, 62.82; H, 5.74; N, 7.38.

EXAMPLE 113

Synthesis of 1-(2-trifluoromethylbenzyl)-2-(3,4,5-trimethoxyphenyl)- 6-[2-(N,N-diisopropylamino)ethoxy]benzimidazole The title compound was prepared by reacting the compound of Example 104 with 2-(N,N-diisopropylamino)ethyl chloride essentially as previously described. mp 184° C., MS 585, NMR, IR.

Analysis for $C_{32}H_{38}F_3N_3O_4$: Theory: C, 65.63; H, 6.54; N, 7.18. Found: C, 65.67; H, 6.42; N, 7.35.

EXAMPLE 114

Synthesis of 1-(2-bromobenzyl)-2-(3,4,5-trimethoxyphenyl)-6-hydroxybenzimidazole The title compound was prepared essentially as described in Example 104 except that 2-bromobenzyl bromide was employed in place of 2-trifluoromethylbenzyl bromide. mp 208° C., NMR, IR, MS 468, 470.

Analysis for $C_{23}H_{21}BrN_2O_4$: Theory: C, 58.86; H, 4.51; N, 5.97. Found: C, 58.61; H, 4.81; N, 6.12.

EXAMPLE 115

Synthesis of 1-(2-bromobenzyl)-2-(3,4,5-trimethoxyphenyl)-6-[2-(piperidin-1-yl)ethoxy]benzimidazole The title compound was prepared by reacting the compound of Example 114 with 2-(piperidin-1-yl)ethyl chloride essentially as previously described. mp 145° C., NMR, MS 579, 581, IR.

Analysis for $C_{30}H_{34}BrN_3O_4$: Theory: C, 62.07; H, 5.90; N, 7.24. Found: C, 61.86; H, 5.91; N, 7.08.

EXAMPLE 116

Synthesis of 1-(2-bromobenzyl)-2-(3,4,5-trimethoxyphenyl)-6-[2-(N,N-dimethylamino)propoxy]benzimidazole The title compound was prepared by reacting the compound of Example 114 with 2-(N,N-dimethylamino)propyl chloride essentially as previously described. mp 152° C., NMR, IR, MS 553, 555.

Analysis for $C_{28}H_{32}BrN_3O_4$: Theory: C, 60.65; H, 5.82; N, 7.58. Found: C, 60.85; H, 5.77; N, 7.44.

EXAMPLE 117

Synthesis of 1-(2-bromobenzyl)-2-(3,4,5-trimethoxyphenyl)-6-[2-(N, N-dimethylamino)ethoxy]benzimidazole The title compound was prepared by reacting the compound of Example 114 with 2-(N,N-dimethylamino)ethyl chloride essentially as previously described. mp 152° C., NMR, IR, MS 539, 541.

Analysis for $C_{27}H_{30}BrN_3O_4$: Theory: C, 60.00; H, 5.59; N, 7.77. Found: C, 59.83; H, 5.63; N, 7.54.

EXAMPLE 118

Synthesis of 1-(2-bromobenzyl)-2-(3,4,5-trimethoxyphenyl)-6-[3-(N, N-dimethylamino)propoxy]benzimidazole The title compound was prepared by reacting the compound of Example 114 with 3-(N,N-dimethylamino)propyl chloride essentially as previously described. mp 141° C., NMR, IR, MS 553, 555.

Analysis for $C_{28}H_{32}BrN_3O_4$: Theory: C, 60.65; H, 5.82; N, 7.58. Found: C, 60.49; H, 6.03; N, 7.34.

EXAMPLE 119

Synthesis of 1-(2-bromobenzyl)-2-{3,4,5-trimethoxyphenyl)-6-[2-(N,N-diisopropylamino)ethoxy]benzimidazole The title compound was prepared by reacting the compound of Example 114 with 2-(N,N-diisopropylamino)ethyl chloride essentially as previously described. MS 595, 597.

Analysis for $C_{31}H_{38}BrN_3O_4$: Theory: C, 62.41; H, 6.42; N, 7.04. Found: C, 62.48; H, 6.48; N, 7.03.

EXAMPLE 120

Synthesis of 1-(2-trifluoromethylbenzyl)-2-(3-methylphenyl)- 6-hydroxybenzimidazole The title compound was prepared essentially as described in Example 104, supra, except that 3-methylbenzoyl chloride was employed instead of 3,4,5-trimethoxybenzoyl chloride. mp 233° C., MS 382, IR, NMR.

Analysis for $C_{22}H_{17}F_3N_2O$: Theory: C, 69.10; H, 4.48; N, 7.33. Found: C, 69.40; H, 4.49; N, 7.27.

EXAMPLE 121

Synthesis of 1-(2-trifluoromethylbenzyl)-2-(3-methylphenyl)- 6-[2-(piperidinyl-1-yl)ethoxy]benzimidazole The title compound was prepared essentially as described in Example 105 except that the compound of Example 120 was reacted with 2-(piperidin-1-yl)ethyl chloride. mp 114° C., NMR, IR, MS 493.

Analysis for $C_{29}H_{30}F_3N_3O$: Theory: C, 70.57; H, 6.13; N, 8.51. Found: C, 70.77; H, 6.22; N, 8.50.

EXAMPLE 122

Synthesis of 1-(2-trifluoromethylbenzyl)-2-(3-methylphenyl)- 6-[2-(N,N-dimethylamino)ethoxy]benzimidazole The title compound was prepared essentially as described in Example 107 except that the compound of Example 120 was reacted with 2-(N,N-dimethylamino)ethyl chloride. mp 93° C., NMR, IR, MS 453.

Analysis for $C_{26}H_{26}F_3N_3O$: Theory: C, 68.86; H, 5.78; N, 9.26. Found: C, 69.12; H, 5.79; N, 9.34.

EXAMPLE 123

Synthesis of 1-(2-trifluoromethylbenzyl)-2-(3-methylphenyl)- 6-[2-(N,N-diisopropylamino)ethoxy]benzimidazole The title compound was prepared essentially as described in Example 113 except that the compound of Example 120 was reacted with 2-(N,N-diisopropylamino)ethyl chloride. MS 510.

Analysis for $C_{30}H_{34}F_3N_3O$: Theory: C, 70.71; H, 6.72; N, 8.25. Found: C, 70.48; H, 6.59; N, 8.26.

EXAMPLE 124

Synthesis of 1-(2-trifluoromethylbenzyl)-2-(3-methylphenyl)- 6-[3-(N,N-dimethylamino)propoxy]benzimidazole The title compound was prepared essentially as described in Example 106 except that the compound of Example 120 was reacted with 3-(N,N-dimethylamino)propyl chloride. mp 74° C., NMR, IR, MS 468.

Analysis for $C_{27}H_{28}F_3N_3O$: Theory: C, 69.36; H, 6.04; N, 8.99. Found: C, 69.52; H, 6.10; N, 9.03.

EXAMPLE 125

Synthesis of 1-(2-trifluoromethylbenzyl)-2-(3-methylphenyl)- 6-[1-methyl-2-(N,N-dimethylamino)ethoxy]benzimidazole The title compound was prepared essentially as described above except that the compound of Example 120 was reacted with 1-methyl-2-(N,N-dimethylamino)ethyl chloride, yielding the title product as an oil.

EXAMPLE 126

Synthesis of 1-(2-bromobenzyl)-2-(3-methylphenyl)-6hydroxybenzimidazole

The title compound was prepared essentially as described in Example 114, supra, except that 3-methylbenzoyl chloride was employed instead of 3,4,5-trimethoxybenzoyl chloride. mp 218° C., NMR, IR, MS 392, 394.

Analysis for $C_{21}H_{17}BrN_2O$: Theory: C, 64.13; H, 4.36; N, 7.12. Found: C, 64.23; H, 4.51; N, 6.93.

EXAMPLE 127

Synthesis of 1-(2-bromobenzyl)-2-(3-methylphenyl)-6-[2-(piperidinyl- 1-yl)ethoxy]benzimidazole The title compound was prepared essentially as described in Example 115 except that the compound of Example 126 was reacted with 2-(piperidin-1-yl)ethyl chloride. mp 107° C., NMR, IR, MS 503, 505.

Analysis for $C_{28}H_{30}BrN_3O$: Theory: C, 66.67; H, 5.99; N, 8.33. Found: C, 66.97; H, 6.12; N, 8.19.

EXAMPLE 128

Synthesis of 1-(2-bromobenzyl)-2-(3-methylphenyl)- 6-[2 (N,N-dimethylamino)ethoxy]benzimidazole The title compound was prepared essentially as described in Example 117 except that the compound of Example 126 was reacted with 2-(N,N-dimethylamino)ethyl chloride. mp 71° C., NMR, IR, MS 464, 466.

Analysis for $C_{25}H_{26}BrN_3O$: Theory: C, 64.66; H, 5.64; N, 9.05. Found: C, 64.58; H, 5.58; N, 9.04.

EXAMPLE 130

Synthesis of 1-{2-bromobenzyl)-2-(3-methylphenyl)-6-[3-(N,N-dimethylamino)propoxy]benzimidazole The title compound was prepared essentially as described in Example 116 except that the compound of Example 126 was reacted with 3-(N,N-dimethylamino)propyl chloride. MS 479.

Analysis for $C_{26}H_{28}BrN_3O$: Theory: C, 65.27; H, 5.90; N, 8.78. Found: C, 64.99; H, 5.85; N, 8.66.

EXAMPLE 131

Synthesis of 1-(2-bromobenzyl)-2-(3-methylphenyl)-6-[1-methyl- 2-(N, N-dimethylamino)ethoxy]benzimidazole The title compound was prepared essentially as described above except that the compound of Example 126 was reacted with 1-methyl-2-(N,N-dimethylamino)ethyl chloride.

EXAMPLE 132

Synthesis of 1-(2-trifluoromethylbenzyl)-2-(3,4-dimethylphenyl)- 6-hydroxybenzimidazole The title compound was prepared essentially as described in Example 104 except that 3,4,-dimethylbenzoyl chloride was employed instead of 3,4,5-trimethoxybenzoyl chloride. mp 178° C., NMR, IR, MS 396.

Analysis for $C_{23}H_{19}F_3N_2O$: Theory: C, 69.69; H, 4.83; N, 7.07. Found: C, 69.40; H, 4.87; N, 6.90.

The following compounds were prepared essentially as described supra, except that the compound of Example 132 was employed as a starting material.

EXAMPLE 133

1-(2-trifluoromethylbenzyl)-2-(3,4-dimethylphenyl)-6-[2-(piperidin- 1-yl)ethoxy]benzimidazole. mp 131° C., NMR, MS 507, IR.

Analysis for $C_{30}H_{32}F_3N_3O$: Theory: C, 70.99; H, 6.35; N, 8.28. Found: C, 70.70; H, 6.23; N, 8.42.

EXAMPLE 134

1-(2-trifluoromethylbenzyl)-2-(3,4- dimethylphenyl)-6-[2-(N,N-dimethylamino)ethoxy]benzimidazole. mp 87° C., MS 467, NMR, IR.

Analysis for $C_{27}H_{28}F_3N_3O$: Theory: C, 69.36; H, 6.04; N, 8.99. Found: C, 69.42; H, 6.01; N, 8.91.

EXAMPLE 135

1-(2-trifluoromethylbenzyl)-2-(3,4-dimethylphenyl)-6-[2-(N,N-diisopropylamino)ethoxy]benzimidazole. mp 121° C., NMR, IR, MS 524.

Analysis for $C_{31}H_{36}F_3N_3O$: Theory: C, 71.11; H, 6.93; N, 8.03. Found: C, 71.34; H, 6.96; N, 8.26.

EXAMPLE 136

1-(2-trifluoromethylbenzyl)-2-(3,4-dimethylphenyl)-6-[2-(N,N-dimethylamino)propoxy]benzimidazole. MS 481.

Analysis for $C_{28}H_{30}F_3N_3O$: Theory: C, 69.84; H, 6.28; N, 8.73. Found: C, 70.24; H, 6.33; N, 8.55.

EXAMPLE 136A 1-(2-trifluoromethylbenzyl)-2-(3,4-dimethylphenyl)-6-[1-methyl-2-(N,N-dimethylamino)ethoxy]benzimidazole MS 481.

Analysis for $C_{28}H_{30}F_3N_3O$: Theory: C, 69.84; H, 6.28; N, 8.73. Found: C, 69.61; H, 6.35; N, 8.50.

EXAMPLE 137

1-(2-bromomethylbenzyl)-2-(3,4-dimethylphenyl)-6-hydroxybenzimidazole

The title compound was prepared essentially as described in Example 114, supra, except that 3,4-dimethylbenzoyl chloride was employed instead of 3,4,5-trimethoxybenzoyl chloride. mp 213° C., MS 406, 408, NMR, IR.

Analysis for $C_{22}H_{19}BrN_2O$: Theory: C, 64.56; H, 5.17; N, 6.84. Found: C, 64.76; H, 4.95; N, 6.62.

The following compounds were prepared essentially as described supra, except that the compound of Example 138 was employed as a starting material.

EXAMPLE 138

1-(2-trifluoromethylbenzyl)-2-(3,4-dimethylphenyl)-6-[3-(N,N-dimethylamino)propoxy]benzimidazole Analysis for $C_{27}H_{30}BrN_3O$: Theory: C, 65.85; H, 6.14; N, 8.53. Found: C, 66.12; H, 6.20; N, 8.49.

EXAMPLE 139

1-(2-bromobenzyl)-2-(3,4-dimethylphenyl)-6-[2-(piperidin-1-yl)ethoxy]benzimidazole. mp 137° C., NMR, IR, MS 517, 519.

Analysis for $C_{29}H_{32}BrN_3O$: Theory: C, 67.18; H, 6.72; N, 8.10. Found: C, 67.45; H, 6.30; N, 8.01.

EXAMPLE 140

1-(2-bromobenzyl)-2-(3,4-dimethylphenyl)-6-[2-(N,N-dimethylamino)ethoxy]benzimidazole. mp 102° C., IR, NMR, MS 478, 479, 480.

Analysis for $C_{26}H_{28}BrN_3O$: Theory: C, 65.27; H, 5.90; N, 8.78. Found: C, 65.43; H, 5.88; N, 8.75.

EXAMPLE 141

1-(2-bromobenzyl)-2-(3,4-dimethylphenyl)-6-[2-(N,N-diisopropylamino)ethoxy]benzimidazole MS 533,535.

Analysis for $C_{30}H_{36}BrN_3O$: Theory: C, 67.41; H, 6.79; N, 7.86. Found: C, 67.36; H, 6.60; N, 7.93.

EXAMPLE 142

1 -(2-bromobenzyl)-2-(3,4-dimethylphenyl)-6-[2-(N,N-dimethylamino)propoxy]benzimidazole. MS 491, 493.

Analysis for $C_{27}H_{30}BrN_3O$: Theory: C, 65.85; H, 6.14; N, 8.53. Found: C, 66.07; H, 6.18; N, 8.54.

EXAMPLE 142A 1-(2-bromobenzyl)-2-(3,4-dimethylphenyl)-6-[1-methyl-2-(N,N-dimethylamino)ethoxy]benzimidazole. MS 491, 493.

Analysis for $C_{27}H_{30}BrN_3O$: Theory: C, 65.85; H, 6.14; N, 8.53. Found: C, 65.74; H, 6.20; N, 8.32.

EXAMPLE 143

1 -(2-bromobenzyl)-2-(3,4-dimethylphenyl)-6-[3-(N,N-dimethylamino)propoxy]benzimidazole. MS 491, 493.

Analysis for $C_{11}H_{14}N_2O_4S$: Theory: C, 65.85; H, 6.14; N, 8.53. Found: C, 66.12; H, 6.20; N, 8.49.

EXAMPLE 145

1-(2-bromomethylbenzyl)-2-(3,5-dimethylphenyl)-6-hydroxybenzimidazole

The title compound was prepared essentially as described in Example 114, supra, except that dimethylbenzoyl chloride was employed instead of 3,4,5-trimethoxybenzoyl chloride. mp 213° C., MS 406, 408, NMR, IR.

Analysis for $C_{22}H_{19}BrN_2O$: Theory: C, 64.88; H, 4.70; N, 6.88. Found: C, 64.74; H, 4.80; N, 7.01.

The following compounds were prepared essentially as described supra, except that the compound of Example 145 was employed as a starting material.

EXAMPLE 146

1-(2-bromobenzyl)-2-(3,5-dimethylphenyl)-6-[2-(piperidin-1-yl)ethoxy]benzimidazole IR, NMR, MS 517, 519, mp 112° C.

Analysis for $C_{29}H_{32}BrN_3 \cdot 0.5\ H_2O$: Theory: C, 66.03; H, 6.31; N, 7.97. Found: C, 66.17; H, 6.50; N, 7.46.

EXAMPLE 147

1-(2-bromobenzyl)-2-(3,5-dimethylphenyl)-6-[2-(N,N-dimethylamino)ethoxy]benzimidazole MS 477,479.

Analysis for $C_{26}H_{28}BrN_3O \cdot H_2O$: Theory: C, 62.90; H, 6.09; N, 8.46. Found: C, 63.09; H, 5.95; N, 8.45.

EXAMPLE 148

1-(2-bromobenzyl)-2-(3,5-dimethylphenyl)-6-[1-methyl-2-(N,N-dimethylamino)ethoxy]benzimidazole. mp 78° C., NMR, IR, MS 491, 493.

Analysis for $C_{27}H_{30}BrN_3O$: Theory: C, 65.85; H, 6.14; N, 8.53. Found: C, 66.05; H, 6.15; N, 8.80.

EXAMPLE 149

1-(2-bromobenzyl)-2-(3,5-dimethylphenyl)-6-[2-(N,N-diisopropylamino)ethoxy]benzimidazole MS 534, 536.

Analysis for $C_{30}H_{36}BrN_3O$: Theory: C, 67.41; H, 6.79; N, 7.86. Found: C, 67.34; H, 6.87; N, 7.62.

EXAMPLE 150

1-(2-bromobenzyl)-2-(3,5-dimethylphenyl)-6-[3-(N,N-dimethylamino)propoxy]benzimidazole. MS 491, 493.

Analysis for $C_{27}H_{30}BrN_3O$: Theory: C, 65.85; H, 6.14; N, 8.53. Found: C, 65.68; H, 6.19; N, 8.53.

EXAMPLE 151

1-phenyl-2-[3-[2-(piperidin-1-yl)ethoxy]phenyl]-benzimidazole

The title compound was prepared by reacting the compound of Example 34 with 2-(piperdin-1-yl)ethyl chloride in acetone and potassium carbonate as previously described. mp 68° C., IR, NMR, MS 397.

Analysis for $C_{26}H_{27}N_3O$: Theory: C, 78.56; H, 6.85; N, 10.57. Found: C, 78.41; H, 6.90; N, 10.45.

EXAMPLE 152

1-phenyl-2-[4-[2-(piperidin-1-yl)ethoxy]phenyl]-benzimidazole

The title compound was prepared by reacting the compound of Example 29 with 2-(piperdin-1-yl)ethyl chloride in acetone and potassium carbonate as previously described. mp 107° C., NMR, MS 397.

Analysis for $C_{26}H_{27}N_3O$: Theory: C, 78.56; H, 6.85; N, 10.57. Found: C, 78.79; H, 7.12; N, 10.51.

EXAMPLE 153

1-phenyl-2-[4-[3-(piperidin-1-yl)propoxy]phenyl]-benzimidazole

The title compound was prepared by reacting the compound of Example 29 with 3-(piperdin-1-yl)propyl chloride in acetone and potassium carbonate as previously described. mp 86° C., NMR, MS 412.

Analysis for $C_{27}H_{29}N_3O$: Theory: C, 78.80; H, 7.10; N, 10.21. Found: C, 79.01; H, 7.18; N, 10.20.

EXAMPLE 154

Synthesis of 1-phenyl-2-(3,4-dimethylphenyl)-6-hydroxybenzimidazole

The title compound was prepared by first reacting 1-chloro-3,4-dinitrobenzene (100 g, 0.50 mole) with aniline (140 ml, 1.54 moles) in ethanol (95%, 550 ml). This reaction mixture was stirred at room temperature for about 72 hours. The resulting 1-chloro-3-phenylamino-4-nitrobenzene was purified by first filtering the orange crystals, followed by washing with hexanes. The crystals were then dried at 80° C. for about 4 hours. Additional product was recovered from the hexanes filtrate by recrystallizing from ethanol.

The 1-chloro-3-phenylamino-4-nitrobenzene was then reacted with two molar equivalents of sodium methoxide, the sodium methoxide being prepared essentially as described in Kottenhahn, et al., *Journal of Organic Chemistry*, 28:3114 (1963). Metallic sodium (5.0 g, 217 mmol) was added slowly to methanol (400 ml). After all of the sodium had gone into solution, the 1-chloro-3-phenylamino-4-nitrobenzene was added and the red-orange solution was heated to reflux and maintained at that temperature overnight. The gold crystals of 1-methoxy-3-phenylamino- 4-nitrobenzene were recovered by filtration, washed with water (2 liters) and dried in vacuo.

The nitro group of the above-described intermediate was then reduce to an amino group by catalytic hydrogenation using a palladium on activated carbon catalyst, essentially as previously described, resulting in 3-phenylamino-4-methoxyaniline with was then reacted with 3,4-dimethylbenzoyl chloride as previously described. This intermediate was then cyclized to the corresponding benzimidazole with phosphorous oxychloride as previously described to yield 1-phenyl-2-(3,4-dimethylphenyl)-6-methoxybenzimidazole.

This intermediate was then reacted with hydrobromic acid (48%) and glacial acetic acid under nitrogen atmosphere to cleave the methoxy group from the 6-position of the benzimidazole. The resulting title compound was purified by adding the reaction mixture to one liter of water and extracting with methylene chloride (3×500 ml). The organic fractions were combined, dried over magnesium sulfate and the solvents were removed in vacuo to yield reddish solid crystals. The crystals were washed with water (3×250 ml) to remove excess hydrobromic acid and then dried, followed by washing with diethyl ether (2×250 ml) and drying in vacuo. mp 251° C., IR, NMR, MS 314.

Analysis for $C_{21}H_{18}N_2O$: Theory: C, 80.23; H, 5.77; N, 8,91. Found: C, 79.98; H, 5.77; N, 8.94.

EXAMPLE 155

1-phenyl-2-(3,4-dimethylphenyl)-6-[2-(piperidin-1-yl)ethoxy]benzimidazole

The title compound was prepared by reacting the compound of Example 154, supra, with 2-(piperidin-1-yl)ethyl chloride as previously described. NMR, IR, MS 425, mp 111° C.

Analysis for $C_{28}H_{31}N_3O \cdot 0.5\ H_2O$: Theory: C, 77.39; H, 7.42; N, 9.67. Found: C, 77.38; H, 7.24; N, 10.36.

The following compounds were prepared essentially as described above:

EXAMPLE 156

1-Benzyl-2-phenylbenzimidazole

EXAMPLE 157

1-(1-Diethylaminopent-4-yl)-2-(3-nitrophenyl)benzimidazole

EXAMPLE 158

1-(1-Diethylaminopent-4-yl)-2-(4-methoxyphenyl)benzimidazole

EXAMPLE 159

1-(1-Dimethylaminoethyl)-2-phenylbenzimidazole

EXAMPLE 160

1-(1-Dimethylaminopropyl)-2-benzylbenzimidazole

EXAMPLE 161

1-(4-chlorophenylmethyl)-2-(4-chlorophenylmethyl)benzimidazole. mp 89°–90° C.

EXAMPLE 162

1-phenyl-2-(4-chlorophenyl)-6-methoxybenzimidazole. mp 171°–172.5° C.

EXAMPLE 163

1-phenyl-2-(4-chlorophenyl)-5-(1-ethylaminoethyl)benzimidazole, (Z)-2-butenedioic acid salt. mp 228° C.

EXAMPLE 164

1-phenyl-2-(4-chlorophenyl)-6-chlorobenzimidazole. mp 210°–212° C.

EXAMPLE 165

1-phenyl-2-(4-chlorophenyl)-6-(imidazol-1-yl)benzimidazole. mp 223° C.

EXAMPLE 166

1-phenyl-2-(4-chlorophenyl)-5-nitrobenzimidazole. mp 194° C.

EXAMPLE 167

1-phenyl-2-(4- chlorophenyl)-6-hydroxyethylaminobenzimidazole. mp 225° C.

EXAMPLE 168

1-phenyl-2-(4-chlorophenyl)-5-(1-aminoethyl)benzimidazole, (Z)-2-butenedioic acid salt. mp 206° C.

EXAMPLE 169

1-phenyl-2-(4-chlorophenyl)-6-(N-isopropylcarbonyl-N-butylamino)benzimidazole. bp 213°–220° C.

EXAMPLE 170

1-phenyl-2-(4-chlorophenyl)-5-acetylbenzimidazole. mp 159° C.

EXAMPLE 171

1-phenyl-2-(4-chlorophenyl)-5-(2-hydroxyethyl)benzimidazole. mp 165° C.

EXAMPLE 172

1-phenyl-2-(4-chlorophenyl)-6-[2-(piperidin-1-yl)ethoxy]benzimidazole. mp 138°–140.

EXAMPLE 173

1-phenyl-2-(4-chlorophenyl)-6-[3-(N,N-dimethylamino)propoxy]benzimidazole. mp 126° C.

EXAMPLE 174

1-phenyl-2-(4-hydroxyphenyl)-6-hydroxybenzimidazole, hydrochloride. mp 212° C.

The biological activity of many of the compounds of the present invention was evaluated employing an initial screening assay which rapidly and accurately measured the inhibition of β-amyloid peptide in a whole cell assay.

β-amyloid peptide naturally occurs as a series of peptides which are 39 to 43 amino acids long, with the shorter, more soluble forms being present in cerebrovascular deposits and the longer forms being found primarily in senile plaques. F. Prelli, et al., *Journal of Neurochemistry*, 51:648–651 (1988). The primary structure of the 43 amino acid long peptide (β1–43) is depicted in SEQ ID NO:1:

Asp Ala Glu Phe Arg His Asp Ser Gly Tyr Glu Val His His Gln 15
Lys Leu Val Phe Phe Ala Glu Asp Val Gly Ser Asn Lys Gly Ala 30
Ile Ile Gly Leu Met Val Gly Gly Val Val Ile Ala Thr 43

Even though the full length peptide of SEQ ID NO:1: has sufficient solubility in water for the following experiments, for the purposes of convenience, a more water-soluble form of the peptide is often desired. For that reason, the following examples were performed using peptides containing just the first 40 amino acids of the β-amyloid peptide (β1–40). The sequence of this preferred peptide is SEQ ID NO:2:

Asp Ala Glu Phe Arg His Asp Ser Gly Tyr Glu Val His His Gln 15
Lys Leu Val Phe Phe Ala Glu Asp Val Gly Ser Asn Lys Gly Ala 30
Ile Ile Gly Leu Met Val Gly Gly Val Val 40

It is understood by those in the art that other fragments of β-amyloid peptide, comprising amino-truncated, carboxy-truncated, or internal deletions, or any combination of these, as well as conservative variants of these peptides, may be employed in this invention so long as that peptide fragment demonstrates the requisite neurotoxicity.

While the peptide of SEQ ID NO:1 and SEQ ID NO:2 are referred to as β-amyloid peptide throughout this document, in the body of literature concerning this field, this peptide is alternatively referred to as β-amyloid protein, amyloid β peptide, amyloid βA4, β protein, amyloid A4, β-peptide, and other such names.

β-Amyloid Peptide Production Inhibition (Cellular Assay)

Two cell lines (human kidney cell line 293 and Chinese hamster ovary cell line CHO) were stably transfected with the gene for APP751 containing the double mutation $Lys_{651}$-$Met_{652}$ to $Asn_{651}$-$Leu_{652}$ (APP-751 numbering) commonly called the Swedish mutation using the method described in Citron, et al., Nature 360:672–674 (1992). The transfected cell lines were designated as 293 751 SWE and CHO 751 SWE, and were plated in Corning 96 well plates at $2.5 \times 10^4$ or $1 \times 10^4$ cells per well respectively in Dulbecco's minimal essential media (DMEM) plus 10% fetal bovine serum. Following overnight incubation at 37° C. in an incubator equilibrated with 10% carbon dioxide ($CO_2$), the media were removed and replaced with 200 μl per well of media containing a macrolide. After a two hour pretreatment period, the media were again removed and replaced with fresh media containing the aspartyl protease inhibitor and the cells were incubated for an additional two hours.

Macrolide stocks were prepared in dimethylsulfoxide such that at the final concentration used in the treatment, the concentration of dimethylsulfoxide did not exceed 0.5%. After treatment, plates were centrifuged at 1200 rpm for five minutes at room temperature to pellet cellular debris from the conditioned media. From each well, 100 μl of conditioned media were transferred into an ELISA plate precoated with antibody 266 against β-amyloid peptide(13–28) and stored at 4° C. overnight. An ELISA assay employing labelled antibody 6C6 (against β-amyloid peptide-1-16) was run the next day to measure the amount of β-amyloid peptide produced.

Cytotoxic effects of the compounds were measured by a modification of the method of Hansen, et al., *Journal of Immunological Methods*, 119:203–210 (1989). To the cells remaining in the tissue culture plate, was added 25 μl of a 3-(4,5-dimethylthiazol-2-yl)2,5-diphenyltetrazolium bromide (MTT) stock solution (5 mg/ml) to a final concentration of 1 mg/ml. Cells were incubated at 37° C. for one hour, and cellular activity was stopped by the addition of an equal volume of MTT lysis buffer (20% w/v sodium dodecylsulfate in 50% DMF, pH 4.7). Complete extraction was achieved by overnight shaking at room temperature. The difference in the $OD_{562nm}$ and the OD650nm was measured in a $UV_{max}$ microplate reader as an indicator of the cellular viability.

The results of the β-amyloid peptide ELISA were fit to a standard curve and expressed as ng/ml β-amyloid peptide. In order to normalize for cytotoxicity, these β-amyloid peptide results were divided by the MTT results and expressed as a percentage of the results from a drug-free control.

In repeated experiments using the above assay, compounds of the present invention have shown significant inhibition of β-amyloid peptide production without demonstrating increased cytotoxicity.

In another assay to better study the effects of these substituted benzimidazoles on whole animals some of the above compounds are administered in vivo to guinea pigs by an intraperitoneal route at 1 mg/kg/day. The individual compound being tested is administered in four 0.25 mg/kg doses separated by one hour. One hour after the last of the four injections, the amount of β-amyloid peptide in the cerebrospinal fluid is measured and compared to control animals in which no such compound is administered.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Active Ingredient | 15.0 mg |
| Starch | 407.0 mg |

| Ingredient | Quantity (mg/capsule) |
|---|---|
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by refernce.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method of treating a condition associated with β-amyloid peptide-associated neurotoxicity, which method comprises administering to a mammal in need of said treatment a compound of the formula

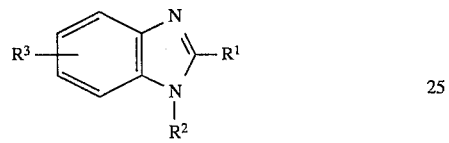

wherein:

$R^1$ is hydrogen, $C_1$-$C_{12}$ alkyl, $C_1$-$C_6$ alkoxy, phenyl, $C_3$-$C_8$ cycloalkyl, naphthyl, phenyl-($C_1$-$C_6$ alkylidenyl)-, naphthyl-($C_1$-$C_6$ alkylidenyl)-, phenyl-($C_1$-$C_6$ alkoxy)-, or naphthyl-($C_1$-$C_6$ alkoxy)-, any one of which phenyl, naphthyl, or $C_3$-$C_8$ cycloalkyl groups may be optionally substituted with one, two, or three moieties independently selected from group consisting of hydroxy, halo, $C_1$-$C_6$ alkyl, $C_1$-$C_6$ alkoxy, trifluoromethyl, nitro, amino, cyano, $C_1$-$C_6$ alkylamino, and $C_1$-$C_6$ alkylthio;

$R^2$ is hydrogen, $C_1$-$C_{12}$ alkyl, $C_1$-$C_6$ alkoxy, phenyl, $C_3$-$C_8$ cycloalkyl, naphthyl, phenyl-($C_1$-$C_6$ alkylidenyl)-, naphthyl-($C_1$-$C_6$ alkylidenyl)-, phenyl-($C_1$-$C_6$ alkoxy)-, or naphthyl-($C_1$-$C_6$ alkoxy)-, any one of which phenyl, naphthyl, or $C_3$-$C_8$ cycloalkyl, groups may be optionally substituted with one, two, or three moieties independenly selected from group consisting of phenyl-($C_1$-$C_6$ alkylidenyl)-, napthyl-($C_1$-$C_6$ alkylidenyl)-, phenyl-($C_1$-$C_6$ alkoxy)-, naphthyl-($C_1$-$C_6$ alkoxy)-, hydroxy, halo, $C_1$-$C_6$ alkyl, $C_1$-$C_6$ alkoxy, trifluoromethyl, nitro, amino, cyano, $C_1$-$C_6$ alkylamino, and $C_1$-$C_6$ alkylthio;

$R^3$ is hydrogen, nitro, $C_1$-$C_6$ alkanoyl, amino, $C_1$-$C_6$ alkyl, $C_1$-$C_6$ alkoxy, $C_3$-$C_8$ cycloalkyl, halo, $C_1$-$C_6$ alkylthio, hydroxy-($C_1$-$C_6$ alkylidenyl)-, hydroxy-($C_1$-$C_6$ alkylidenyl)amino-, $R^4R^5N$-, $R^4R^5N$-($C_1$-$C_6$ alkylidenyl)-, $R^4R^5N$-($C_1$-$C_6$ alkoxy)-, hydroxy-($C_1$-$C_6$ alkyl-, amino($C_1$-$C_6$ alkylidenyl)-, or trifluoromethyl, where $R^4$ and $R^5$ are independently selected from the group consisting of $C_1$-$C_6$ alkyl, $C_1$-$C_6$ alkoxy, $C_1$-$C_6$ alkanoyl, aryl, aryl($C_1$-$C_6$ alkylidenyl)-, and hydrogen or $R^4$ and $R^5$ combine to form $C_3$-$C_8$ cycloalkyl, any one of which alkyl or alkoxy groups may be substituted with one or more halo, amino, or nitro, and any one of which aryl groups may be substituted with one, two, or three moieties independently selected from group consisting of hydroxy, halo, $C_1$-$C_6$ alkyl, $C_1$-$C_6$ alkoxy, trifluoromethyl, nitro, amino, cyano, $C_3$-$C_8$ cycloalkyl, $C_1$-$C_6$ alkylamino, and $C_1$-$C_6$ alkylthio;

with the proviso that not more than one of $R^1$ and $R^2$ may be hydrogen;

or a pharmaceutically acceptable salt thereof.

2. A method as claimed in claim 1 employing a compound wherein $R^2$ is phenyl ($C_1$-$C_6$ alkylidenyl)-, heterocyclic ($C_1$-$C_6$ alkylidenyl)-, unsaturated heterocyclic ($C_1$-$C_6$ alkylidenyl)-, or a substituted derivative thereof, or a pharmaceutically acceptable salt thereof.

3. A method as claimed in claim 2 employing a compound wherein $R^2$ is benzyl, phenyl, substituted phenyl, or substituted benzyl or a pharmaceutically acceptable salt thereof.

4. A method as claimed in claim 3 employing a compound wherein the $R^2$ is benzyl optionally substituted with halo, $C_1$-$C_6$ alkoxy, or trifluoromethyl,or a pharmaceutically acceptable salt thereof.

5. A method as claimed in claim 4 employing a compound wherein the benzyl is optionally substituted at the 2-position or a pharmaceutically acceptable salt thereof.

6. A method as claimed in claim 5 employing a compound wherein $R^1$ is phenyl substituted with one, two, or three moieties selected from the group consisting of halo, hydroxy, $C_1$-$C_6$ alkoxy, $C_1$-$C_6$ alkyl, and nitro, or a pharmaceutically acceptable salt thereof.

* * * * *

UNITED STATES PATENT AND TRADEMARK OFFICE
CERTIFICATE OF CORRECTION

PATENT NO. : 5,552,426
DATED : September 3, 1996
INVENTOR(S) : William H. W. Lunn, et al It is certified that error appears in the above-identified patent and that said Letters Patent is hereby corrected as shown below:

Column 58, line 45, "trifluoromethyl,or a" should read -- trifluoromethyl, or a --.

Signed and Sealed this

Third Day of March, 1998

Attest:

Attesting Officer

BRUCE LEHMAN
Commissioner of Patents and Trademarks